(12) United States Patent
Lee et al.

(10) Patent No.: US 6,512,002 B2
(45) Date of Patent: Jan. 28, 2003

(54) METHODS OF TREATMENT FOR PREMATURE EJACULATION IN A MALE

(75) Inventors: Andrew G. Lee; Wesley W. Day, both of Old Lyme; David D. Thompson, Gales Ferry, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/757,423

(22) Filed: Jan. 10, 2001

(65) Prior Publication Data

US 2001/0044434 A1 Nov. 22, 2001

Related U.S. Application Data

(60) Provisional application No. 60/175,704, filed on Jan. 12, 2000.

(51) Int. Cl.$^7$ ..................... A61K 31/40; A61K 31/405
(52) U.S. Cl. ..................... 514/427; 514/415; 514/410; 514/429; 514/428
(58) Field of Search ................... 514/427, 428, 514/415, 410, 429

(56) References Cited

U.S. PATENT DOCUMENTS

| | | |
|---|---|---|
| 5,552,412 A | 9/1996 | Cameron et al. |
| 5,889,042 A | 3/1999 | MacLean et al. |
| 5,948,809 A | 9/1999 | Chiu et al. |
| 6,107,331 A | 8/2000 | MacLean et al. |
| 6,107,964 A | 8/2000 | Hirabe |
| 6,153,622 A | 11/2000 | Cameron et al. |
| 6,204,286 B1 | 3/2001 | Cameron et al. |

FOREIGN PATENT DOCUMENTS

| | | | |
|---|---|---|---|
| EP | 792641 A1 | * 3/1997 | .......... A61K/31/40 |
| EP | 0793961 | 9/1997 | |

OTHER PUBLICATIONS

Bartlik, B. et al., *Psychiatric Annals* (1999), Jan., 29:1, Sexual Disorders in Women, 46–52, *Medications With the Potential to Enhance Sexual Responsivity in Women*.

Berman, J. R., et al., *Female Sexual Dysfunction: Incidence, Pathophysiology, Evaluation, and Treatment Options*, Urology, vol. 5, (1999), pp. 385–391.

* cited by examiner

*Primary Examiner*—Minna Moezie
*Assistant Examiner*—S. Jiang
(74) *Attorney, Agent, or Firm*—Peter C. Richardson; Gregg C. Benson; Todd M. Crissey

(57) ABSTRACT

This invention relates to methods and pharmaceutical compositions useful in the treatment of conditions that are responsive to the elevation of testosterone levels in the body and the use of estrogen agonists/antagonists for the manufacture of medicaments for the treatment of conditions that are responsive to the elevation of testosterone levels in the body. The compositions are comprised of an estrogen agonist/antagonist and a pharmaceutically acceptable vehicle, carrier or diluent. These compositions are effective in treating male subject sexual dysfunction and timidity in female subjects including post-menopausal women and are effective in increasing libido in female subjects including post-menopausal women. In the case of male subject sexual dysfunction, the compositions may also include a compound which is an elevator of cyclic guanosine 3',5'-monophosphate (cGMP). Additionally, the compositions are effective in other conditions whose etiology is a result of testosterone deficiency or which can be ameliorated by increasing testosterone levels within the body. Methods of the invention include the treatment of conditions that are responsive to elevation of testosterone levels such as treating male subject sexual dysfunction and timidity in female subjects including post-menopausal women and the increase of libido of female subjects including post-menopausal women. The methods of treatment are effective while substantially reducing the concomitant liability of adverse effects associated with testosterone administration.

5 Claims, No Drawings

METHODS OF TREATMENT FOR PREMATURE EJACULATION IN A MALE

CROSS REFERENCE TO RELATED APPLICATION

This application claims priority of U.S. provisional application No. 60/175,704, filed Jan. 12, 2000.

FIELD OF THE INVENTION

This invention relates to compositions and methods for treating conditions responsive to testosterone administration including male subject sexual dysfunction, lowered libido in female subjects including post-menopausal women and timidity in female subjects including post-menopausal women. The compositions and methods utilize estrogen agonist/antagonist compounds.

BACKGROUND OF THE INVENTION

Testosterone, the principal androgen, is synthesized in the testis, the ovary, and the adrenal cortex. In the circulation, testosterone serves as a prohormone for the formation of two classes of steroids: 5α-reduced androgens, which act as the intracellular mediators of most androgen action, and estrogens, which enhance some androgenic effects and block others. Thus the net effect of the action of endogenous androgens is the sum of the effects of the secreted hormone (testosterone), its 5α-reduced metabolite (dihydrotestosterone, and its estrogenic derivative (estradiol). Adequate amounts of these hormones are required for proper physical development and physiological homeostasis. When diminished or absent from the body, pathological conditions can arise in the body due to a testosterone deficiency which are treatable by testosterone replacement. Additional conditions can be treated or ameliorated through the supplementation of endogenous testosterone.

Conditions responsive to testosterone elevation may arise in women as a result of menopause. Menopause occurs naturally at an average age of 50 to 51 years in the USA. As ovaries age, response to pituitary gonadotropins (follicle-stimulating hormone [FSH] and luteinizing hormone [LH]) decreases, initially resulting in shorter follicular phases (thus, shorter menstrual cycles), fewer ovulations, decreased progesterone production, and more irregularity in cycles. Eventually, the follicle fails to respond and does not produce estrogen. The transitional phase, during which a woman passes out of the reproductive stage, begins before menopause. It is termed the climacteric or perimenopause, although many persons refer to it as menopause.

Premature menopause refers to ovarian failure of unknown cause that occurs before age 40. It may be associated with smoking, living at high altitude, or poor nutritional status. Artificial menopause may result from oophorectomy, chemotherapy, radiation of the pelvis, or any process that impairs ovarian blood supply.

Symptoms of the climacteric range from nonexistent to severe. Hot flushes (flashes) and sweating secondary to vasomotor instability affect 75% of women. Most women have hot flushes for more than 1 year, and 25 to 50% for more than 5 years. The woman feels warm or hot and may perspire, sometimes profusely. The skin, especially of the head and neck, becomes red and warm. The flush, which may last from 30 sec to 5 min, may be followed by chills. Vasomotor symptoms of the hot flush coincide with the onset of LH pulses, but not every increase in LH is associated with a hot flush, suggesting that hypothalamic control of LH pulses is independent of that of flushes. This independence is confirmed by the occurrence of hot flushes in women who have had pituitary failure and do not secrete LH and/or FSH.

Psychologic and emotional symptoms—including fatigue, irritability, insomnia, inability to concentrate, depression, memory loss, headache, anxiety, and nervousness and timidity can occur. Sleep disruption by recurrent hot flushes contributes to fatigue and irritability. Intermittent dizziness, paresthesias, palpitations, and tachycardia may also occur. Nausea, constipation, diarrhea, arthralgia, myalgia, cold hands and feet, and weight gain are also common.

The large reduction in estrogen leads to profound changes in the lower genital tract; eg, the vaginal mucosa and vulvar skin become thinner, the normal bacterial flora changes, and the labia minora, clitoris, uterus, and ovaries decrease in size. Inflammation of the vaginal mucosa (atrophic vaginitis) can cause the mucosa to have a strawberry appearance and can lead to urinary frequency and urgency, vaginal dryness, and dyspareunia. Women tend to lose pelvic muscle tone and to develop urinary incontinence, cystitis, and vaginitis.

In men, conditions responsive to testosterone elevation may be caused by primary hypogonadism (congenital or acquired) including testicular failure due to cryptorchidism, bilateral torsion, orchitis, vanishing testis syndrome, or orchidectomy, Klinefelter's syndrome, chemotherapy, or toxic damage from alcohol or heavy metals. Also, in men, these conditions may be caused by secondary, i.e., hypogonadotropic, hypogonadism (congenital or acquired)—idiopathic gonadotropin or luteinizing hormone-releasing hormone (LHRH) deficiency, or pituitary-hypothalamic injury from tumors, trauma, or radiation. These men have low serum testosterone concentrations without associated elevation in gonadotropins.

The sexual response cycle is mediated by a delicate, balanced interplay between the sympathetic and parasympathetic nervous systems. Vasocongestion is largely mediated by parasympathetic (cholinergic) outflow; orgasm is predominantly sympathetic (adrenergic). Ejaculation is almost entirely sympathetic; emission involves sympathetic and parasympathetic stimulation. These responses are easily inhibited by cortical influences or by impaired hormonal, neural, or vascular mechanisms. β-Adrenergic blockers may desynchronize emission, ejaculation, and perineal muscle contractions during orgasm, and serotonin agonists frequently interfere with desire and orgasm.

Disorders of sexual response may involve one or more of the cycle's phases. Generally, both the subjective components of desire, arousal, and pleasure and the objective components of performance, vasocongestion, and orgasm are disturbed, although any may be affected independently.

Sexual dysfunctions may be lifelong (no effective performance ever, generally due to intrapsychic conflicts) or acquired (after a period of normal function); generalized or limited to certain situations or certain partners; and total or partial.

Penile erection is initiated by neuropsychologic stimuli that ultimately produce vasodilation of the sinusoidal spaces and arteries within the paired corpora cavernosa. Erection is normally preceded by sexual desire (or libido), which is regulated in part by androgen-dependent psychological factors. Although nocturnal and diurnal spontaneous erections are suppressed in men with androgen deficiency, erections may continue for long periods in response to erotic stimuli. Thus, continuing action of testicular androgens appears to be required for normal libido but not for the erectile mechanism itself.

The penis is innervated by sympathetic, parasympathetic, and somatic fibers. Somatic fibers in the dorsal nerve of the penis form the afferent limb of the erectile reflex by transmitting sensory impulses from the penile skin and glans to the S2-S4 dorsal root ganglia via the pudendal nerve. Unlike the corpuscular-type endings in the penile shaft skin, most afferents in the glans terminate in free nerve endings. The efferent limb begins with parasympathetic preganglionic fibers from S2-S4 that pass in the pelvic nerves to the pelvic plexus. Sympathetic fibers emerging from the intermediolateral gray areas of T11-L2 travel through the paravertebral sympathetic chain ganglia, superior hypogastric plexus, and hypogastric nerves to enter the pelvic plexus along with parasympathetic fibers. Somatic efferent fibers from S3-S4 that travel in the pudendal nerve to the ischiocavernosus and bulbocavernosus muscles and postganglionic sympathetic fibers that innervate the smooth muscle of the epididymis, vas deferens, seminal vesicle, and internal sphincter of the bladder mediate rhythmic contraction of these structures at the time of ejaculation.

Autonomic nerve impulses, integrated in the pelvic plexus, project to the penis through the cavernous nerves that course along the posterolateral aspect of the prostate before penetrating the pelvic floor muscles immediately lateral to the urethra. Distal to the membranous urethra, some fibers enter the corpus spongiosum, while the remainder enter the corpora cavernosa along with the terminal branches of the pudendal artery and exiting cavernous veins.

The brain exerts an important modulatory influence over spinal reflex pathways that control penile function. A variety of visual, auditory, olfactory, and imaginative stimuli elicit erectile responses that involve cortical, thalamic, rhinencephalic, and limbic input to the medial preoptic-anterior hypothalamic area, which acts as an integrating center. Other areas of the brain, such as the amygdaloid complex, may inhibit sexual function.

Although the parasympathetic nervous system is the primary effector of erection, the transformation of the penis to an erect organ is a vascular phenomenon. In the flaccid state the arteries, arterioles, and sinusoidal spaces within the corpora cavernosa are constricted due to sympathetic-mediated contraction of smooth muscle in the walls of these structures. The venules between the sinusoids and the dense tunica albuginea surrounding the cavernosa open freely to the emissary veins. Erection begins when relaxation of the sinusoidal smooth muscles leads to dilation of the sinusoids and a decrease in peripheral resistance, causing a rapid increase in arterial blood flow through internal pudendal and cavernosa arteries. Expansion of the sinusoidal system compresses the venules against the interior surface of the tunica albuginea, resulting in venous occlusion. The increase in intracorporeal pressure leads to rigidity; less than complete expansion of the sinusoidal spaces leads to less than complete rigidity.

Erection occurs when adrenergic-induced sinusoid tone is antagonized by sacral parasympathetic stimulation that produces sinusoidal relaxation primarily by synthesis and release of the nonadrenergic-noncholinergic (NANC) neurotransmitter nitric oxide (NO). The contribution of acetylcholine-dependent release of NO from the vascular endothelium is uncertain. In vitro electrical stimulation of isolated corpus cavernosum strips (with or without endothelium) produces sinusoidal relaxation by release of neurotransmitters within nerve terminals that is resistant to adrenergic and cholinergic blockers. Inhibitors of the synthesis of NO or of guanosine monophosphate (GMP), as well as nitric oxide scavengers, block sinusoidal relaxation. A variety of neuropeptides found in corporal tissues, including vasoactive intestinal peptide (VIP) and calcitonin gene-related peptide (CGRP), produce tumescence when injected into the penis but have uncertain physiologic roles. Elevators of cGMP stimulate or facilitate tumescence. Certain compounds that block or inhibit phosphodiesterase enzymes that act on cGMP have been found to be an orally active therapy for impotence. Norepinephrine plays an important role in the adrenergic mechanism of detumescence.

Seminal emission and ejaculation are under control of the sympathetic nervous system. Emission results from alpha-adrenergic-mediated contraction of the epididymis, vas deferens, seminal vesicles, and prostate which causes seminal fluid to enter the prostatic urethra. Concomitant closure of the bladder neck prevents retrograde flow of semen into the bladder, and antegrade ejaculation results from contraction of the muscles of the pelvic floor including the bulbocavernosus and ischiocavernosus muscles.

Orgasm is a psychosensory phenomenon in which the rhythmic contraction of the pelvic muscles is perceived as pleasurable. Orgasm can occur without either erection or ejaculation or in the presence of retrograde ejaculation.

Detumescence after orgasm and ejaculation is incompletely understood. Presumably, active tone in the vessels of the sinusoidal spaces is restored by contraction (probably adrenergic-mediated) of smooth muscles, which decreases the inflow of blood to the penis and promotes emptying of the erectile tissue. Following orgasm, there is a refractory period that varies in duration with age, physical condition, and psychic factors and during which erection and ejaculation are inhibited (McConnell J. D. and Wilson J. D., *Impotence,* Chapter 51, in *Harrison's Principles of Internal Medicine,* 14th ed., 1998).

Men with sexual dysfunction present with a variety of complaints, either singly, or in combination: loss of desire (libido), inability to initiate or maintain an erection, ejaculatory failure, premature ejaculation, or inability to achieve orgasm. Sexual dysfunction can be secondary to systemic disease or its treatment, to specific disorders of the urogenital or endocrine systems, or to psychological disturbance. It was previously thought that the majority of men with erectile impotency had a psychological etiology for the dysfunction, but it is now believed that most impotent men have a component of underlying organic disease. Impotence is the failure to achieve erection, ejaculation, or both.

A decrease in sexual desire, or libido, may be due to androgen deficiency (arising from either pituitary or testicular disease), psychological disturbance, or to some types of prescribed or habitually abused drugs. The possibility of androgen deficiency can be tested by measurement of plasma testosterone and gonadotropin. The minimal level of testosterone required for normal erectile function remains unknown. Hypogonadism may also result in the absence of emission, secondary to decreased secretion of ejaculate by the seminal vesicles and prostate.

The organic causes of erectile impotence can be grouped into endocrine, drug, local, neurologic, and vascular causes. With the exception of severe depression, men with psychogenic impotence usually have normal nocturnal and early morning erections. From early childhood through the eighth decade, erections occur during normal sleep. This phenomenon, termed nocturnal penile tumescence (NPT), occurs during rapid eye movement sleep, and the total time of NPT averages 100 min per night. Consequently, if the impotent man gives a history of rigid erections under any circumstances (often when awakening in the morning), the efferent neurologic and circulatory systems that mediate erection are intact.

If the history of nocturnal erections is questionable, measurements of NPT can be made formally with the use of a strain gauge in a sleep laboratory, or informally attached to a recorder, by snap gauge or home monitor. Although false-negative and false-positive results are possible, this procedure helps to differentiate psychogenic and organic impotence. Patients with vasculogenic impotence may have some degree of penile tumescence without the development of adequate rigidity, which may result in a false-positive NPT test. An alternative to NTP testing is the visual sexual stimulation test, which utilizes videotaped erotic material in a laboratory setting to monitor erection by strain gauge.

For the treatment of male subject sexual dysfunction, the compositions of the present invention can be administered either singly or in combination with cGMP elevating agents. Agents which elevate cGMP levels are well known and can work through any of several mechanisms. Agents which selectively inhibit an enzyme predominantly involved in cGMP breakdown, for example a cGMP-dependent phosphodiesterase constitute one example.

In particular, cyclic guanosine 3',5'-monophosphate phosphodiesterase (cGMP PDE) inhibitors are widely known as cardiovascular agents for the treatment of conditions such as angina, hypertension, and congestive heart failure. More recently cGMP PDE inhibitors capable of inhibiting type V phosphodiesterase (cGMP $PDE_V$) have been found to be effective for the treatment of impotence, importantly by oral administration. See, for example, PCT/EP94/01580, published as WO 94/28902 which designates, inter alia, the United States, and which is herein incorporated by reference.

The compositions and methods of the present invention act to cure, ameliorate, or prevent pathological conditions that are responsive to the elevation of testosterone levels within the body. Elevation of testosterone in the body can typically be measured in the blood, serum, plasma or at the site of action. Not being bound by any single theory, it is believed that administration of the compositions of the invention results in an elevation of testosterone levels within the body to cure, ameliorate or prevent conditions responsive to such elevations of testosterone levels.

SUMMARY OF THE INVENTION

This invention relates to pharmaceutical compositions useful in the treatment of conditions that are responsive to the elevation of testosterone levels in the body. The compositions are comprised of an estrogen agonist/antagonist and a pharmaceutically acceptable carrier, vehicle or diluent. These compositions are effective in treating male subject sexual dysfunction and timidity in female subjects including post-menopausal women and are effective in increasing libido in female subjects including post-menopausal women. In the case of male subject sexual dysfunction, the compositions may also include a compound which is an elevator of cyclic guanosine 3',5'-monophosphate (cGMP). Additionally, the compositions are effective in other conditions whose etiology is a result of testosterone deficiency or which can be ameliorated by increasing testosterone levels within the body.

A second aspect of the invention relates to methods of treating conditions that are responsive to treatment which elevates testosterone levels within the body. These methods include treatment of male subject sexual dysfunction and timidity in female subjects including post-menopausal women and treatment which increases libido in female subjects including post-menopausal women. In the case of the treatment of male subject sexual dysfunction, the method may include the co-administration of an elevator of cGMP.

A third aspect of the invention is that the compositions and methods of treatment for conditions responsive to testosterone elevation substantially reduces the concomitant liability of adverse effects associated with testosterone administration.

As a fourth aspect, the present invention provides kits for use by a consumer afflicted with or susceptible to physical conditions that are responsive to the elevation of testosterone levels in the body. The kit comprises a) a pharmaceutical composition comprising an estrogen agonist/antagonist and a pharmaceutically acceptable carrier, vehicle or diluent; and b) instructions describing a method of using the pharmaceutical composition for treating physical conditions that are responsive to the elevation of testosterone levels in the body. The instructions may also indicate that the kit is for the treatment of testosterone-responsive conditions while substantially reducing the concomitant liability of adverse effects associated with testosterone administration. The conditions responsive to testosterone elevation include male subject sexual dysfunction and timidity in female subjects including post-menopausal women and the increase of libido in female subjects including post-menopausal women. This invention also provides a kit comprising a therapeutically effective amount of an estrogen agonist/antagonist and a pharmaceutically acceptable carrier, vehicle or diluent in a first unit dosage form and, optionally, a) a therapeutically effective amount of a cGMP elevator and a pharmaceutically acceptable carrier, vehicle or diluent in a second unit dosage form.

As a fifth aspect, the present invention provides for the use of estrogen agonists/antagonists for the manufacture of a medicament for the treatment of conditions that are responsive to treatment that elevates testosterone levels within the body. These conditions include male subject sexual dysfunction and timidity in female subjects including post-menopausal women and the increase libido in female subjects including post-menopausal women and which may be treated by the medicament without the concomitant liability of adverse effects associated with testosterone administration.

DETAILED DESCRIPTION OF THE INVENTION

The present invention relates to compositions and methods for the treatment of conditions responsive to testosterone elevation. Unless otherwise specified, the following terms have the meanings as defined below:

"Treatment" as used herein includes preventative (e.g., prophylactic), curative or palliative treatment and "treating" as used herein also includes preventative, curative and palliative treatment.

A "subject" is an animal including the human species that is treatable with the compositions, methods and kits of the present invention. The term "subject" or "subjects" is intended to refer to both the male and female gender unless one gender is specifically indicated.

"Co-administration" of a combination of a estrogen agonist/antagonist and/or a cGMP elevator means that these components can be administered together as a composition or as part of the same, unitary dosage form. "Co-administration" also includes administering a estrogen agonist/antagonist and/or a cGMP elevator separately but as part of the same therapeutic treatment program or regimen. The components need not necessarily be administered at essentially the same time, although they can if so desired. Thus "co-administration" includes, for example, administering a estrogen agonist/antagonist and/or a cGMP elevator as separate dosages or dosage forms, but at the same time. "Co-administration" also includes separate administration at different times and in any order. For example, where appropriate a patient may take one or more component(s) of the treatment in the morning and the one or more of the other component(s) at night.

"Conditions responsive to elevation of testosterone levels" include those conditions caused by testosterone deficiency. In childhood, androgen deficiency has few consequences, but if it occurs at the expected time of puberty, secondary sexual development is impaired. Patients with hypogonadism have poor muscle development, a high-pitched voice, inadequate phallic and testicular growth, small scrotum, sparse pubic and axillary hair, and absent body hair. They may develop gynecomastia and attain eunuchoidal body proportions because of delayed fusion of the epiphyses and continued long bone growth. In adulthood, androgen deficiency has varied manifestations depending on the degree and length of deficiency. Decreased libido, potency, and overall strength are common. Testicular atrophy, fine wrinkling of the skin around the eyes and lips, and sparse body hair may occur with long-standing hypogonadism. Osteopenia and gynecomastia may also develop. Additional indications responsive to testosterone treatment include decreased libido in female subjects including post-menopausal women, timidity in female subjects including post-menopausal women, stimulation of erythropoiesis and treatment of anemia, treatment of hereditary angiomeurotic edema, short stature, carcinoma of the breast, stimulation of muscle growth and increase in nitrogen balance.

"Timidity" is further defined as inappropriate fearfulness of difficult circumstances or social settings or inappropriate shyness attributable to the post-menopausal condition. Timidity and other social tendencies can be assessed using health-related quality of life (HRQL) measurement questionnaires implemented in a double-blind placebo-controlled clinical study of suitable size. One HRQL instrument is the MOS 36-Item Short Form Health Survey (MOS SF-36) which was developed by A. L. Stewart, R. Hays and J. E. Ware (Ware, J. E. and Sherbourne C. D., *Med Care;* 30:473, 1992, Stewart A. L., et al., *JAMA;* 262:907, 1989, Tarlov A. R., et al., *JAMA;* 262:925,1989, McHorney C. A., et al., *Med Care;* 32:40,1994). The MOS SF-36 collects information from the patient on the areas of physical functioning; role limitations due to physical health problems; bodily pain; social functioning; general mental health; role limitations due to emotional problems, vitality, energy or fatigue and general health perceptions. Another HRQL measurement instrument is the Nottingham Health Profile (Hunt S. M., et al., *Soc Sci Med;* 15 A:221, 1981, Hunt S. M., et al., *J Royal Coll Gen Pract;* 35:185,1985)—a two section, 46 item scale that measures physical, social, and emotional health problems and their impact on functioning.

"Male subject sexual dysfunction" includes decreased libido (hypoactive sexual desire disorder) in which sexual fantasies and desire for sexual activity are persistently or recurrently diminished or absent, causing marked distress or interpersonal difficulties. Also included are male subject orgasmic disorder characterized by a persistent or recurrent delay in or absence of orgasm after normal sexual arousal, and decreased potency (erectile dysfunction).

"Decreased libido in female subjects including post-menopausal women" is a hypoactive sexual desire disorder, as defined in male subject sexual disorder, in which sexual fantasies and desire for sexual activity are persistently or recurrently diminished or absent in a post-menopausal woman.

"Adverse effects associated with testosterone" include polycythemia (and increased risk of stroke), gynecomastia, prostatic enlargement, sodium and water retention, impairment of hepatic function, hypercholesteremia and suppression of high-density lipoprotein concentrations.

The term "female subjects including post-menopausal women" is defined to include female animals including humans and, among humans, not only women of advanced age who have passed through menopause, but also women who have undergone hysterectomy or for some other reason have suppressed estrogen production, such as those who have undergone long-term administration of corticosteroids, suffer from Cushions' syndrome or have gonadal dysgenesis.

An "estrogen agonist/antagonist" is a compound that affects some of the same receptors that estrogen does, but not all, and in some instances, it antagonises or blocks estrogen. It is also known as a "selective estrogen receptor modulator" (SERM). Estrogen agonists/antagonists may also be referred to as antiestrogens although they have some estrogenic activity at some estrogen receptors. Estrogen agonists/antagonists are therefore not what are commonly referred to as "pure antiestrogens". Antiestrogens that can also act as agonists are referred to as Type I antiestrogens. Type I antiestrogens activate the estrogen receptor to bind tightly in the nucleus for a prolonged time but with impaired receptor replenishment (Clark et al., *Steroids* 22:707, 1973, Capony et al., *Mol Cell Endocrinol,* 3:233, 1975).

Preferred estrogen agonists/antagonists of the present invention include the compounds described in U.S. Pat. No. 5,552,412. Those compounds are described by formula (I) given below:

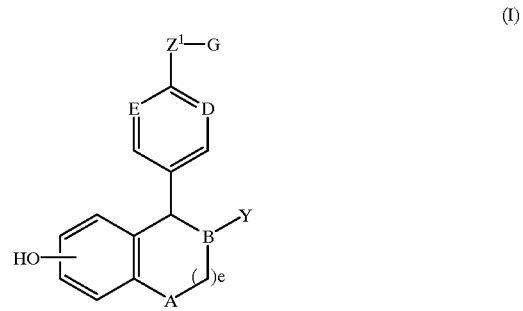

(I)

wherein:
A is selected from $CH_2$ and NR;
B, D and E are independently selected from CH and N; Y is
(a) phenyl, optionally substituted with 1–3 substituents independently selected from $R^4$;
(b) naphthyl, optionally substituted with 1–3 substituents independently selected from $R^4$;
(c) $C_3$–$C_8$ cycloalkyl, optionally substituted with 1–2 substituents independently selected from $R^4$;
(d) $C_3$–$C_8$ cycloalkenyl, optionally substituted with 1–2 substituents independently selected from $R^4$;

(e) a five membered heterocycle containing up to two heteroatoms selected from the group consisting of —O—, —NR$^2$— and —S(O)$_n$—, optionally substituted with 1–3 substituents independently selected from R$^4$;

(f) a six membered heterocycle containing up to two heteroatoms selected from the group consisting of —O—, —NR$^2$— and —S(O)$_n$— optionally substituted with 1–3 substituents independently selected from R$^4$; or (g) a bicyclic ring system consisting of a five or six membered heterocyclic ring fused to a phenyl ring, said heterocyclic ring containing up to two heteroatoms selected from the group consisting of —O—, —NR$^2$— and —S(O)$_n$—, optionally substituted with 1–3 substituents independently selected from R$^4$;

Z$^1$ is
(a) —(CH$_2$)$_p$W(CH$_2$)$_q$—;
(b) —(OCH$_2$)$_p$CR$^5$R$^6$—;
(c) —(OCH$_2$)$_p$W(CH$_2$)$_q$—;
(d) —OCHR$^2$CHR$^3$—; or
(e) —SCHR$^2$CHR$^3$—;

G is
(a) —NR$^7$R$^8$;

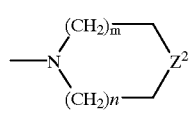
(b)

wherein n is 0, 1 or 2; m is 1, 2 or 3; Z$^2$ is —NH—, —O—, —S—, or —CH$_2$—; optionally fused on adjacent carbon atoms with one or two phenyl rings and, optionally independently substituted on carbon with one to three substituents and, optionally, independently on nitrogen with a chemically suitable substituent selected from R$^4$; or (c) a bicyclic amine containing five to twelve carbon atoms, either bridged or fused and optionally substituted with 1–3 substituents independently selected from R$^4$; or

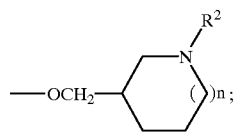

Z$^1$ and G in combination may be
W is
(a) —CH$_2$—;
(b) —CH=CH—;
(c) —O—;
(d) —NR$^2$;
(e) —S(O)$_n$—;

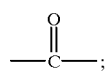
(f)

(g) —CR$^2$(OH)—;
(h) —CONR$^2$—;
(i) —NR$^2$CO—;

(j)

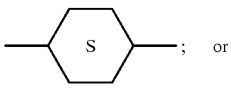
; or (k) —C≡C—;

R is hydrogen or C$_1$–C$_6$ alkyl;
R$^2$ and R$^3$ are independently
(j)(a) hydrogen; or
(j)(b) C$_1$–C$_4$ alkyl;
R$^4$ is
(a) hydrogen;
(b) halogen;
(c) C$_1$–C$_6$ alkyl;
(d) C$_1$–C$_4$ alkoxy;
(e) C$_1$–C$_4$ acyloxy;
(f) C$_1$–C$_4$ alkylthio;
(g) C$_1$–C$_4$ alkylsulfinyl;
(h) C$_1$–C$_4$ alkylsulfonyl;
(i) hydroxy (C$_1$–C$_4$)alkyl;
(j) aryl (C$_1$–C$_4$)alkyl;
(k) —CO$_2$H;
(l) —CN;
(m) —CONHOR;
(n) —SO$_2$NHR;
(o) —NH$_2$;
(p) C$_1$–C$_4$ alkylamino;
(q) C$_1$–C$_4$ dialkylamino;
(r) —NHSO$_2$R;
(s) —NO$_2$;
(t) —aryl; or
(u) —OH;

R$^5$ and R$^6$ are independently C$_1$–C$_8$ alkyl or together form a C$_3$–C$_{10}$ carbocyclic ring;
R$^7$ and R$^8$ are independently
(a) phenyl;
(b) a C$_3$–C$_{10}$ carbocyclic ring, saturated or unsaturated;
(c) a C$_3$–C$_{10}$ heterocyclic ring containing up to two heteroatoms, selected from —O—, —N— and —S—;
(d) H;
(e) C$_1$–C$_6$ alkyl; or
(f) form a 3 to 8 membered nitrogen containing ring with R$^5$ or R$^6$;

R$^7$ and R$^8$ in either linear or ring form may optionally be substituted with up to three substituents independently selected from C$_1$–C$_6$ alkyl, halogen, alkoxy, hydroxy and carboxy;

a ring formed by R$^7$ and R$^8$ may be optionally fused to a phenyl ring;

e is 0, 1 or2;
m is 1, 2 or3;
n is 0, 1 or2;
p is 0, 1, 2or3;
q is 0, 1, 2or3;

and optical and geometric isomers thereof; and nontoxic pharmacologically acceptable acid addition salts, N-oxides, esters, quaternary ammonium salts and prodrugs thereof.

By halo is meant chloro, bromo, iodo, or fluoro or by halogen is meant chlorine, bromine, iodine or fluorine.

By alkyl is meant straight chain or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

By alkoxy is meant straight chain or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

The parenthetical negative or positive sign used herein in the nomenclature denotes the direction plane polarized light is rotated by the particular stereoisomer.

Additional preferred compounds of the invention are of the formula (IA):

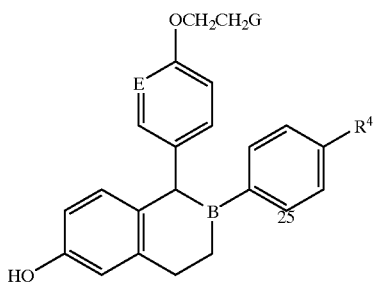
(IA)

wherein G is

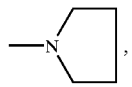,

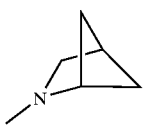

or

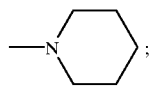;

$R^4$ is H, OH, F, or Cl; and B and E are independently selected from CH and N.

Especially preferred compounds of the invention for the compositions and methods are:
cis-6-(4-fluoro-phenyl)-5-[4-(2-piperidin-1-yl-ethoxy)-phenyl]-5,6,7,8-tetrahydro-naphthalene-2-ol;
(−)-cis-6-phenyl-5-[4-(2-pyrrolidin-1-yl-ethoxy)-phenyl]-5,6,7,8-tetrahydro-naphthalene-2-ol;
cis-6-phenyl-5-[4-(2-pyrrolidin-1-yl-ethoxy)-phenyl]-5,6,7,8-tetrahydro-naphthalene-2-ol;
cis-1-[6'-pyrrolodinoethoxy-3'-pyridyl]-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-[4-(2-piperidin-1-yl-ethoxy)-phenyl]-5,6,7,8-tetrahydro-naphthalene-2-ol; and
1-(4'-pyrrolidinolethoxyphenyl)-2-phenyl-6-hydroxy-1,2,3,4-tetrahydroisoquinoline and pharmaceutically acceptable salts thereof. An especially preferred salt of (−)-cis-6-phenyl-5-[4-(2-pyrrolidin-1-yl-ethoxy)-phenyl]-5,6,7,8-tetrahydro-naphthalene-2-ol is the tartrate salt.

Other preferred estrogen agonists I antagonists are described in U.S. Pat. No. 5,047,431. The structure of these compounds is given by formula (II) below:

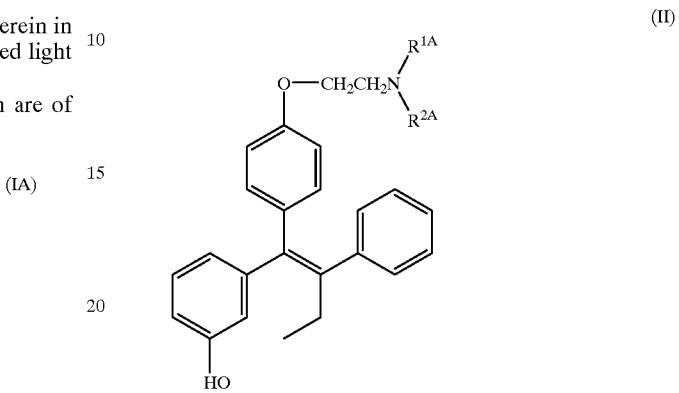
(II)

wherein $R^{1A}$ and $R^{2A}$ may be the same or different provided that, when $R^{1A}$ and $R^{2A}$ are the same, each is a methyl or ethyl group, and, when $R^{1A}$ and $R^{2A}$ are different, one of them is a methyl or ethyl group and the other is hydrogen or a benzyl group; and pharmaceutically acceptable salts and prodrugs thereof.

Additional preferred estrogen agonists/antagonists are tamoxifen: (ethanamine, 2-[-4-(1,2-diphenyl-1-butenyl) phenoxy]-N,N-dimethyl, (Z)-2-, 2-hydroxy-1,2,3-propanetricarboxylate(1:1)) and other compounds as disclosed in U.S. Pat. No. 4,536,516; 4-hydroxy tamoxifen (i.e., tamoxifen wherein the 2-phenyl moiety has a hydroxy group at the 4 position) and other compounds as disclosed in U.S. Pat. No. 4,623,660; raloxifene: (methanone, [6-hydroxy-2-(4-hydroxyphenyl)benzo[b]thien-3-yl][4-[2-(1-piperidinyl)ethoxy]phenyl]-,hydrochloride) and other compounds as disclosed in U.S. Pat. Nos. 4,418,068, 5,393,763, 5,457,117, 5,478,847 and 5,641,790; toremifene: (ethanamine, 2-[4-(4-chloro-1,2-diphenyl-1-butenyl) phenoxy]-N,N-dimethyl-, (Z)-, 2-hydroxy-1,2,3-propanetricarboxylate (1:1) and other compounds as disclosed in U.S. Pat. Nos. 4,696,949 and 4,996,225; centchroman: 1-[2-[[4-(-methoxy-2,2, dimethyl-3-phenyl-chroman-4-yl)-phenoxy]-ethyl]-pyrrolidine and other compounds as disclosed in U.S. Pat. No. 3,822,287; idoxifene: pyrrolidine, 1-[-[4-[[1-(4-iodophenyl)-2-phenyl-1-butenyl] phenoxy]ethyl] and other compounds as disclosed in U.S. Pat. No. 4,839,155; 6-($^4$-hydroxy-phenyl)-5-[4-(2-piperidin-1-yl-ethoxy)-benzyl]-naphthalen-2-ol and other compounds as disclosed in U.S. Pat. No. 5,484,795; and {4-[2-(2-aza-bicyclo[2.2.1]hept-2-yl)-ethoxy]-phenyl}-[6-hydroxy-2-(4)-hydroxy-phenyl)-benzo[b]thiophen-3-yl]-methanone and other compounds as disclosed in published international application WO 95/10513. Other preferred compounds include GW 5638 and GW 7604. The synthesis of these compounds is described in Willson et al., *J. Med. Chem.*, 1994;37:1550–1552.

Further preferred estrogen agonists/antagonists include EM-652 (as shown in the formula designated herein as formula (III) and EM-800 (as shown in the formula designated herein as formula (IV)). The synthesis of EM-652 and EM-800 and the activity of various enantiomers is described in Gauthier et al., *J. Med. Chem.*, 1997;40:2117–2122.

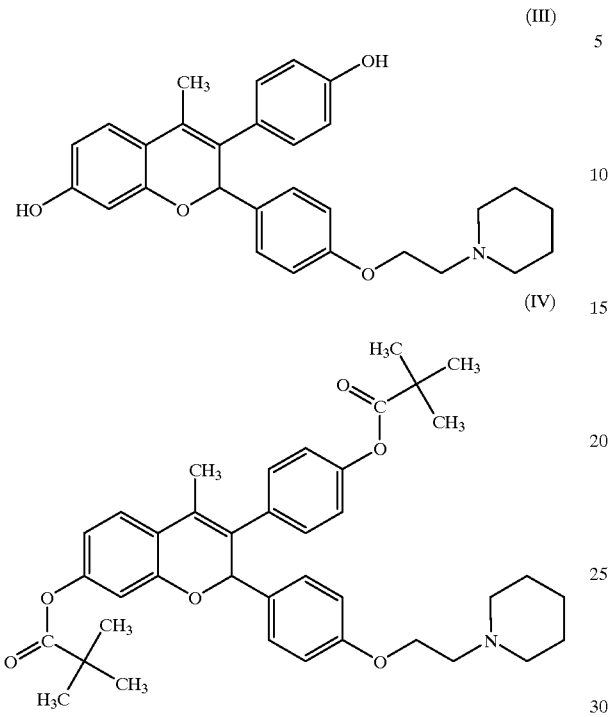

(III)

(IV)

Further preferred estrogen agonists/antagonists include TSE 424 and other compounds disclosed in U.S. Pat. No. 5,998,402, U.S. Pat. No. 5,985,910, U.S. Pat. No. 5,780,497, U.S. Pat. No. 5,880,137, and European Patent Application EP 0802183 A1 including the compounds described by the formulae designated herein as formulae V and VI, below:

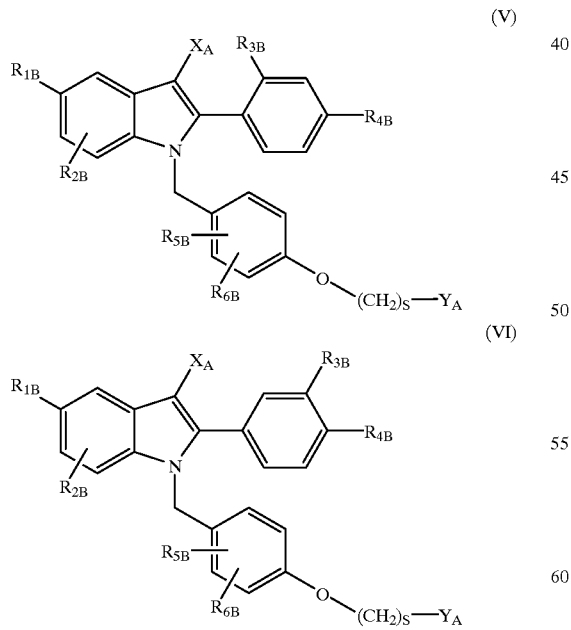

(V)

(VI)

wherein:
R1B is selected from H, OH or the $C_1$–$C_{12}$ esters (straight chain or branched) or $C_1$–$C_{12}$ (straight chain or branched or cyclic) alkyl ethers thereof, or halogens; or $C_1$–$C_4$ halogenated ethers including trifluoromethyl ether and trichloromethyl ether.

$R_{2B}$, $R_{3B}$, $R_{4B}$, $R_{5B}$, and $R_{6B}$ are independently selected from H, OH or the $C_1$–$C_{12}$ esters (straight chain or branched) or $C_1$–$C_{12}$ alkyl ethers (straight chain or branched or cyclic) thereof, halogens, or $C_1$–$C_4$ halogenated ethers including trifluoromethyl ether and trichloromethyl ether, cyano, $C_1$–$C_6$ alkyl (straight chain or branched), or trifluoromethyl;

$X_A$ is selected from H, $C_1$–$C_6$ alkyl, cyano, nitro, trifluoromethyl, and halogen;

s is 2 or 3;

$Y_A$ is selected from:
a) the moiety:

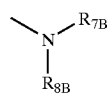

wherein $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$;

b) a five-membered saturated, unsaturated or partially unsaturated heterocycle containing up to two heteroatoms selected from the group consisting of —O—, —NH—, —N($C_1$–$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONHR1B, —$NH_2$, $C_1$–$C_4$ alkylamino, di($C_1$–$C_4$)alkylamino, —$NHSO_2R1B$, —$NHCOR_{1B}$, —$NO_2$, and phenyl optionally substituted with 1–3 ($C_1$–$C_4$)alkyl;

c) a six-membered saturated, unsaturated or partially unsaturated heterocycle containing up to two heteroatoms selected from the group consisting of —O—, —NH—, —N($C_1$–$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_1$, —$NH_2$, $C_1$–$C_4$ alkylamino, di($C_1$–$C_4$)alkylamino, —$NHSO_2R_{1B}$, —$NHCOR_{1B}$, —$NO_2$, and phenyl optionally substituted with 1–3 ($C_1$–$C_4$)alkyl;

d) a seven-membered saturated, unsaturated or partially unsaturated heterocycle containing up to two heteroatoms selected from the group consisting of —O—, —NH—, —N($C_1$–$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONHR$_{1B}$, —$NH_2$, $C_1$–$C_4$ alkylamino, di($C_1$–$C_4$)alkylamino, —NHSO$_2$R$_{1B}$, —NHCOR$_{1B}$, —$NO_2$, and phenyl optionally substituted with 1–3 ($C_1$–$C_4$)alkyl; or e) a bicyclic heterocycle containing from 6–12 carbon atoms either bridged or fused and containing up to two heteroatoms selected from the group consisting of —O—, —NH—, —N($C_1$–$C_4$ alkyl)-, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$—, —CN—, —CONHR$_{1B}$—, —$NH_2$, —N=, $C_1$–$C_4$ alkylamino, di($C_1$–$C_4$)alkylamino, —NHSO$_2$R$_1$B, —NHCOR$_{1B}$, —$NO_2$, and phenyl optionally substituted with 1–3 ($C_1$–$C_4$) alkyl; and optical and geometric isomers thereof; and nontoxic pharmacologically acceptable acid addition salts, N-oxides, esters, quaternary ammonium salts, and prodrugs thereof.

The more preferred compounds of this invention are those having the general structures V or VI, above, wherein:

$R_{1B}$ is selected from H, OH or the $C_1$–$C_{12}$ esters or alkyl ethers thereof, and halogen;

$R_{2B}$, $R_{3B}$, $R_{4B}$, $R_{5B}$, and $R_{6B}$ are independently selected from H, OH or the $C_1$–$C_{12}$ esters or alkyl ethers thereof, halogen, cyano, $C_1$–$C_6$ alkyl, or trihalomethyl, preferably trifluoromethyl, with the proviso that, when $R_{1B}$ is H, $R_{2B}$ is not OH;

$X_A$ is selected from H, $C_1$–$C_6$ alkyl, cyano, nitro, trifluoromethyl, and halogen;

$Y_A$ is the moiety:

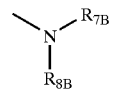

$R_{7B}$ and $R_{8B}$ are selected independently from H, $C_1$–$C_6$ alkyl, or combined by —(CH$_2$)$_w$—, wherein w is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$alkyl), —$NH_2$, $C_1$–$C_4$ alkylamino, $C_1$–$C_4$ dialkylamino, —NHSO$_2$ ($C_1$–$C_4$alkyl), —CO($C_1$–$C_4$alkyl), and —$NO_2$; and optical and geometric isomers thereof; and nontoxic pharmacologically acceptable acid addition salts, N-oxides, esters, quaternary ammonium salts, and prodrugs thereof.

The rings formed by a concatenated $R_{7B}$ and $R_{8B}$, mentioned above, may include, but are not limited to, aziridine, azetidine, pyrrolidine, piperidine, hexamethyleneamine or heptamethyleneamine rings.

The most preferred compounds of structural formulas V and VI, above, are those wherein $R_1B$ is OH; $R_{2B}$–$R_{6B}$ are as defined above; $X_A$ is selected from the group of Cl, $NO_2$, CN, $CF_3$, or $CH_3$; $Y_A$ is the moiety

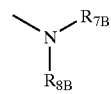

and $R_{7B}$ and $R_{8B}$ are concatenated together as —(CH$_2$)$_t$—, wherein t is an integer of from 4 to 6, to form a ring optionally substituted by up to three subsituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$) alkyl, —$NH_2$, $C_1$–$C_4$ alkylamino, di($C_1$–$C_4$)alkylamino, —NHSO$_2$($C_1$–$C_4$)alkyl, —NHCO($C_1$–$C_4$)alkyl, and —$NO_2$; and optical and geometric isomers thereof; and nontoxic pharmacologically acceptable acid addition salts, N-oxides, esters, quaternary ammonium salts, and prodrugs thereof.

Another preferred compound is TSE-424 as described by the formula designated herein as formula (Va) below:

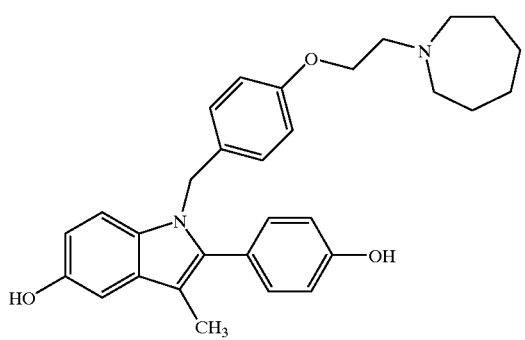

(Va)

The subject invention also includes isotopically-labeled estrogen agonists/antagonists, which are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

Pharmaceutical chemists will easily recognize that physiologically active compounds which have accessible hydroxy groups are frequently administered in the form of pharmaceutically acceptable esters. The literature concerning such compounds, such as estradiol, provides a great number of instances of such esters. The compounds of this invention are no exception in this respect, and can be effectively administered as an ester, formed on the hydroxy groups, just as one skilled in pharmaceutical chemistry would expect. While the mechanism has not yet been investigated, it is believed that esters are metabolically cleaved in the body, and that the actual drug, which such form is administered, is the hydroxy compound itself. It is possible, as has long been known in pharmaceutical chemistry, to adjust the rate or duration of action of the compound by appropriate choices of ester groups.

Certain ester groups are preferred as constituents of the compounds of this invention. The estrogen agonists/antagonists may contain ester groups at various positions as defined herein above, where these groups are represented as COOR$^9$, R$^9$ is $C_1$–$C_{14}$ alkyl, $C_1$–$C_3$ chloroalkyl, $C_1$–$C_3$ fluoroalkyl, $C_5$ –$C_7$ cycloalkyl, phenyl, or phenyl mono- or disubstituted with $C_1$–$C_4$ alkyl, $C_1$–$C_4$ alkoxy, hydroxy, nitro, chloro, fluoro or tri(chloro or fluoro)methyl.

As used herein, the term "effective amount" means an amount of compound of the compositions, kits and methods of the present invention that is capable of inhibiting the symptoms of the described pathological conditions. The specific dose of a compound administered according to this invention will, of course, be determined by the particular circumstances surrounding the case including, for example, the compound administered, the route of administration, the state of being of the patient, and the severity of the pathological condition being treated.

The pharmaceutically acceptable acid addition salts of the compounds of this invention may be formed of the compound itself, or of any of its esters, and include the pharmaceutically acceptable salts which are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid. A preferred salt of (−)-cis-6-phenyl-5-[4-(2-pyrrolidin-1-yl-ethoxy)-phenyl]-5,6,7,8-tetrahydro-naphthalen-2-ol is the D-(−)-tartrate salt.

The compounds of this invention, as discussed above, are very often administered in the form of acid addition salts. The salts are conveniently formed, as is usual in organic chemistry, by reacting the compound of this invention with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it.

The dose of a compound of this invention to be administered to a human is rather widely variable and subject to the judgment of the attending physician. It should be noted that it may be necessary to adjust the dose of a compound when it is administered in the form of a salt, such as a tartrate, the salt forming moiety of which has an appreciable molecular weight. The general range of effective administration rates of the compounds is from about 0.001 mg/day to about 250 mg/day. A preferred rate range is from about 0.010 mg/day to 200 mg/day. Of course, it is often practical to administer the daily dose of compound in portions, at various hours of the day. However, in any given case, the amount of compound administered will depend on such factors as the solubility of the active component, the formulation used and the route of administration.

The route of administration of the compounds of this invention is not critical. It is usually preferred to administer a compound orally for reasons of convenience. However, the compounds may equally effectively be administered percutaneously, or as suppositories for absorption by the rectum or vagina, if desired in a given instance. All of the usual types of compositions may be used, including tablets, chewable tablets, capsules, solutions, parenteral solutions, troches, suppositories and suspensions. Compositions are formulated to contain a daily dose, or a convenient fraction of daily dose, in a dosage unit, which may be a single tablet or capsule or convenient volume of a liquid.

In general, all of the compositions are prepared according to methods usual in pharmaceutical chemistry and by those procedure outlined in the U.S. Pat. Nos. referenced above.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant may be necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums, more particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

The term "prodrug" means compounds that are transformed in vivo to yield a compound of the present invention. The transformation may occur by various mechanisms, such as through hydrolysis in blood. A good discussion of the use of prodrugs is provided by T. Higuchi and W. Stella, "Pro-drugs as Novel Delivery Systems," Vol. 14 of the *A.C.S. Symposium Series,* and in *Bioreversible Carriers in Drug Design,* ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as $(C_1-C_8)$ alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl.

Similarly, if a compound of the present invention comprises an alcohol functional group, a prodrug can be formed by the replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$) alkanoyloxy)ethyl, $(C_1-C_6)$alkoxycarbonyloxymethyl, N-$(C_1-C_6)$alkoxycarbonylaminomethyl, succinoyl, $(C_1-C_6)$ alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, $-P(O)(O(C_1-C_6)alkyl)_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as $R^x$-carbonyl, $R^xO$-carbonyl, $NR^xR^{x'}$-carbonyl where $R^x$ and $R^{x1'}$ are each independently $((C_1-C_{10})$alkyl, $(C_3-C_7)$cycloalkyl, benzyl, or $R^x$-carbonyl is a natural α-aminoacyl or natural α-aminoacyl-natural α-aminoacyl, $-C(OH)C(O)OY^X$ wherein ($Y^X$ is H, $(C_1-C_6)$ alkyl or benzyl), $-C(OY^{X0}) Y^{X1}$ wherein $Y^{X0}$ is $(C_1-C_4)$ alkyl and $Y^{X1}$ is (($C_1-C_6$)alkyl, carboxy($C_1-C_6$)alkyl, amino $(C_1-C_4)$alkyl or mono—N— or di-N,N-$(C_1-C_6)$ alkylaminoalkyl, $-C(Y^{X2}) y^{X3}$ wherein $Y^{X2}$ is H or methyl and $Y^{X3}$ is mono-N- or di-N,N-$(C_1-C_6)$alkylamino, morpholino, piperidin-1-yl or pyrrolidin-1-yl.

For the treatment of male subject sexual dysfunction, cGMP elevator agents may be coadministered with the estrogen agonist/antagonists of the present invention either separately or in a single composition.

Preferred as the cGMP elevator are cGMP PDE inhibitors. cGMP PDE inhibitors which are selective for cGMP PDEs rather than cyclic adenosine 3',5'-monophosphate phosphodiesterases (cAMP PDEs) and/or which are selective inhibitors of the cGMP PDEV isoenzyme are particularly preferred. Such particularly preferred cGMP PDE inhibitors are disclosed in U.S. Pat. Nos. 5,250,534; 5,346,901; 5,272,147, and in the international patent application published as WO 94/28902 designating, inter alia, the U.S., each of which is incorporated herein by reference.

Preferred cGMP PDEV inhibitors include compounds of formula (III):

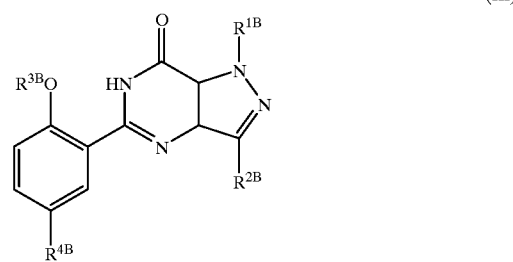

wherein:
$R^{1B}$ is H; $C_1-C_3$ alkyl; $C_1-C_3$ perfluoroalkyl; or $C_3-C_5$ cycloalkyl;

$R^{2B}$ is H; $C_1-C_6$ alkyl optionally substituted with $C_3-C_6$ cycloalkyl; $C_1-C_3$ perfluoroalkyl; or $C_3-C_6$ cycloalkyl;

$R^{3B}$ is $C_1-C_6$ alkyl optionally substituted with $C_3-C_6$ cycloalkyl; $C_1-C_6$ perfluoroalkyl; $C_3-C_5$ cycloalkyl; $C_3-C_6$ alkenyl; or $C_3-C_6$ alkynyl;

$R^{4B}$ is $C_1-C_4$ alkyl optionally substituted with OH, $NR^{5B}$ $R^{6B}$, CN, $CONR^{5B}R^{6B}$ or $CO_2R^{7B}$; $C_2-C_4$ alkenyl optionally substituted with CN, $CONR^{5B} R_{6B}$ or $CO_2R^{7B}$; $C_2-C_4$ alkanoyl optionally substituted with $NR^{5B} R^{6B}$; (hydroxy)$C_2-C_4$ alkyl optionally substituted with $NR^{5B} R^{6B}$ ; $(C_2-C_3$ alkoxy)$C_1-C_2$ alkyl optionally substituted with OH or $NR^{5B} R^{6B}$ ; $CONR^{5B}R_6B$ $CO_2R^{7B}$; halo; $NR^{5B} R^{6B}$; $NHSO_2NR^{5B}R^{6B}$; $NHSO_2R^{8B}$; $SO_2NR^{9B}R^{10B}$ or phenyl, pyridyl, pyrimidinyl, imidazolyl, oxazolyl, thiazolyl, thienyl or triazolyl any of which is optionally substituted with methyl;

$R^{5B}$ and $R^{6B}$ are each independently H or $C_1-C_4$ alkyl, or together with the nitrogen atom to which they are attached form a pyrrolidinyl, piperidino, morpholino, 4-N($R^{11B}$) perazinyl or imidazolyl group wherein said group is optionally substituted with methyl or OH;

$R^{7B}$ is H or $C_1-C_4$ alkyl;

$R^{8B}$ is $C_1-C_3$ alkyl optionally substituted with $NR^{5B} R^{6B}$;

$R^{9B}$ and $R^{10B}$ together with the nitrogen atom to which they are attached form a pyrrolidinyl, piperidino, morpholino or 4N($R^{12B}$) perazinyl group wherein said group is optionally substituted with $C_1$–$C_4$ alkyl, $C_1$–$C_3$ alkoxy, $NR^{13B}R^{14B}$ or $CONR^{13B}R^{14B}$;

$R^{11B}$ is H; $C_1$–$C_3$ alkyl optionally substituted with phenyl; (hydroxy)$C_2$–$C_3$ alkyl; or $C_1$–$C_4$ alkanoyl;

$R^{12B}$ is H; $C_1$–$C_6$ alkyl; ($C_1$–$C_3$ alkoxy)$C_2$–$C_6$ alkyl; (hydroxy)$C_2$–$C_6$ alkyl; ($R^{13B}R^{14B}$N)$C_2$–$C_6$ alkyl; ($R^{13B}R^{14B}$NOC)$C_1$–$C_6$ alkyl; $CONR^{13B}R^{14B}$; $CSNR^{13B}R^{14B}$; or $C(NH)NR^{13B}R^{14B}$; and $R^{13B}$ and $R^{14B}$ are each independently H; $C_1$–$C_4$ alkyl; ($C_1$–$C_3$ alkoxy)$C_2$–$C_4$ alkyl; or (hydroxy)$C_2$–$C_4$ alkyl;

or a pharmaceutically acceptable salt thereof;

or a pharmaceutically acceptable composition containing either entity.

Preferred cGMP $PDE_V$ inhibitors include sildenafil (preferably the citrate salt) {1-[[3-(6,7-dihydro-1-methyl-7-oxo-3-propyl-1 H-pyrazolo[4,3-d]pyrimidin-5-yl) ethoxy-phenyl]sulfonyl]-4-methylpiperazine}, which has the structure of formula (IV):

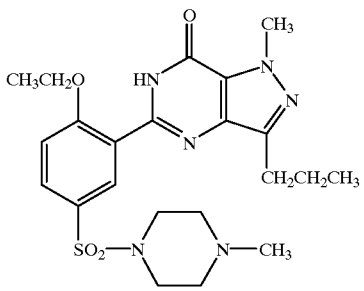

and pharmaceutically acceptable salts thereof, the compound having the structure of formula (V):

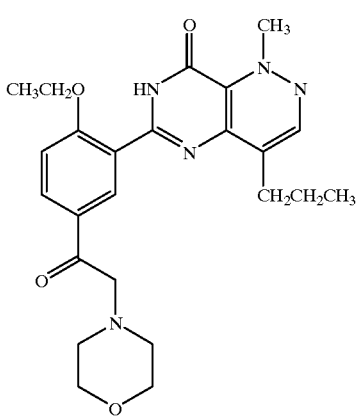

and pharmaceutically acceptable salts thereof, and the compound, 3-ethyl-5-{5-[(4-ethylpiperazino) sulphonyl]-2-(2-methoxyethoxy)pyrid-3-yl}-2-(2-pyridylmethyl)-6,7-dihydro-2H-pyrazolo[4,3-d]pyrimidin-7-one of formula (VI) below:

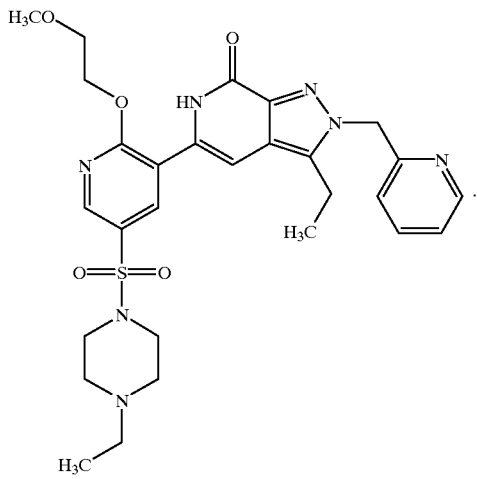

The compound of formula (V) is disclosed, for example, in U.S. Pat. Nos. 5,272,147 and 5,426,107.

Additional suitable cGMP $PDE_V$ inhibitors that can be used in the present invention in combination with an estrogen agonist/antagonist include the pyrazolo [4,3-d] pyrimidin-7-ones disclosed in EP-A-0463756; the pyrazolo [4,3-d]pyrimidin-7-ones disclosed in EP-A-0526004; the pyrazolo [4,3-d]pyrimidin-7-ones disclosed in published international patent application WO 93/06104; the isomeric pyrazolo [3,4-d]pyrimidin-4-ones disclosed in published international patent application WO 93/07149; the quinazolin-4-ones disclosed in published international patent application WO 93/12095; the pyrido [3,2-d] pyrimidin-4-ones disclosed in published international patent application WO 94/05661; the purin-6-ones disclosed in published international patent application WO 94/00453; the pyrazolo [4,3-d]pyrimidin-7-ones disclosed in published international patent application WO 98/49166; the pyrazolo [4,3-d]pyrimidin-7-ones disclosed in published international patent application WO 99/54333; the pyrazolo [4,3-d] pyrimidin-4-ones disclosed in EP-A-0995751; the pyrazolo [4,3-d]pyrimidin-7-ones disclosed in published international patent application WO 00/24745; the pyrazolo [4,3-d] pyrimidin4-ones disclosed in EP-A-0995750; the compounds disclosed in published international application WO 95/19978; the compounds disclosed in published international application WO 99/24433 and the compounds disclosed in published international application WO 93/07124.

Preferred type V phosphodiesterase inhibitors for the use in the present invention include: 5-(2-ethoxy-5-morpholinoacetylphenyl)-1-methyl-3-n-propyl-1,6-dihydro-7H-pyrazolo[4,3-d]pyrimidin-7-one (see EP-A-0526004); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO 99/54333); (+)-3-ethyl-5-[5-(4-ethylpiperazin-1-ylsulphonyl)-2-(2-methoxy-1 (R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1 -methylethyl]oxy) pyridin-3-yl}-2-methyl-2,6-dihydro-7H-pyrazolo[4,3-d] pyrimidin-7-one (see WO 99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1{6-ethoxy-5-[3-ethyl-6,7-dihydro-2-

(2-methoxyethyl)-7-oxo-2H-pyrazolo[4,3d]pyrimidin-5-yl]-3-pyridylsulphonyl}-4-ethylpiperazine (see Example 1 hereinafter); 5-[2-isoButoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see Example 2 hereinafter); 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see Example 3 hereinafter); 5-(5-Acetyl-2-propoxy-3-pyridinyl)-3-ethyl-2-(1-isopropyl-3-azetidinyl)-2,6-dihydro-7H -pyrazolo[4,3-d] pyrimidin-7-one (see Example 4 hereinafter); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see Example 5 hereinafter); (6R, 12aR)-2,3,6,7,12,12a-hexahydro-2-methyl-6-(3,4-methylenedioxyphenyl) -pyrazino[2', 1': 6,1] pyrido[3,4-b]indole-1,4-dione (IC-351), i.e., the compound of examples 78 and 95 of published international application WO 95/19978, as well as the compound of examples 1, 3, 7 and 8; 2-[2-ethoxy-5-(4-ethyl-piperazin-1-yl-1-sulphonyl)-phenyl]-5-methyl-7-propyl-3H-imidazo[5,1-f][1,2,4] triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e., the compound of examples 20, 19, 337 and 336 of published international application WO 99/24433; the compound of example 11 of published international application WO 93/07124 (EISAI); and compounds 3 and 14 from Rotella, D. P., *J. Med. Chem.*, 2000, 43,1257.

Additional cGMP PDE$_V$ inhibitors useful in conjunction with the present invention include: 4-bromo-5-(pyridylmethylamino)-6-[3-(4-chlorophenyl)-propoxy]-3 (2H)pyridazinone; 1-[4-[(1,3-benzodioxol-5-ylmethyl) amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5] imidazo[2,1-b]purin-4(3H)one; furazlocillin; cis-2-hexyl-5-methyl-3,4,5,6a,7,8,9,9a-octahydrocyclopent[4,5]-imidazo [2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; I-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl) amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer) and Sch-51866.

Preferably, the cGMP PDE$_V$ inhibitors have an IC50 for PDE$_V$ at less than 100 nanomolar, more preferably, at less than 50 nanomolar, more preferably still at less than 10 nanomolar.

IC50 values for the cGMP PDEV inhibitors may be determined using established literature methodology, for example as described in EP 0463756-B1 and EP 0526004-A1.

Preferably the cGMP PDE$_V$ inhibitors used in the invention are selective for the PDE$_V$ enzyme. Preferably they are selective over PDE$_{III}$, more preferably over PDE$_{III}$, and PDE$_{IV}$. Preferably, the CGMP PDE$_V$ inhibitors of the invention have a selectivity ratio greater than 100 more preferably greater than 300, over PDE$_{III}$ and more preferably over PDE$_{III}$, and PDE$_{IV}$.

Selectivity ratios may readily be determined by the skilled person. IC$_{50}$ values for the PDE$_{III}$ and PDE$_{IV}$ enzyme may be determined using established literature methodology, see S. A. Ballard et al,. Journal of Urology, 1998, vol.159, pages 2164–2171.

PDE$_V$ SYNTHETIC EXAMPLES

Example 1

2-(Methoxyethyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

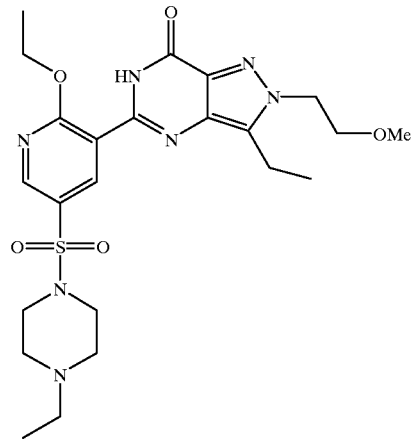

A mixture of the product from stage i) below (0.75 mmol), potassium bis(trimethylsilyl)amide (298 mg, 1.50 mmol) and ethyl acetate (73 microliters, 0.75 mmol) in ethanol (10 ml) was heated at 120° C. in a sealed vessel for 12 hours. The cooled mixture was partitioned between ethyl acetate and aqueous sodium bicarbonate solution, and the layers separated. The organic phase was dried (MgSO$_4$), and evaporated under reduced pressure. The crude product was purified by column chromatography on silica gel using dichloromethane:methanol (98:2) as eluant to afford the title compound, 164 mg; Found : C, 53.18; H, 6.48; N, 18.14; C$_{23}$H$_{33}$N$_7$O$_5$S;0.20C$_2$H$_5$CO$_2$CH$_3$ requires C, 53.21; H, 6.49; N, 18.25% δ (CDCl$_3$): 1.04 (3H, t), 1.40 (3H, t), 1.58 (3H, t), 2.41 (2H, q), 2.57 (4H, m), 3.08 (2H,q),3.14 (4H, m), 3.30 (3H, s), 3.92 (2H, t), 4.46 (2H, t), 4.75 (2H, q), 8.62 (1H, d d), 10.61 (1H, s); LRMS: m/z 520 (M+1)$^+$; mp 161–162° C.

Preparation of Starting Materials
a) Pyridine-2-amino-5-sulphonic acid

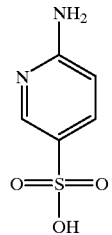

2-Aminopyridine (80 g, 0.85 mol) was added portionwise over 30 minutes to oleum (320 g) and the resulting solution heated at 140° C. for 4 hours. On cooling, the reaction was poured onto ice (200 g) and the mixture stirred in an ice/salt bath for a further 2 hours. The resulting suspension was filtered, the solid washed with ice water (200 ml) and cold IMS (200 ml) and dried under suction to afford the title compound as a solid, 111.3 g; LRMS: m/z 175 (M+1)⁺.

b) pyridine-2-amino-3-bromo-5-sulphonic acid

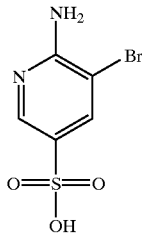

Bromine (99 g, 0.62 mol) was added dropwise over an hour, to a hot solution of the product from stage a) (108 g, 0.62 mol) in water (600 ml) so as to maintain a steady reflux. Once the addition was complete the reaction was cooled and the resulting mixture filtered. The solid was washed with water and dried under suction to afford the title compound, 53.4 g; δ (DMSOd$_6$, 300 MHz): 8.08 (1H, s), 8.14 (1H, s); LRMS : m/z 253 (M)⁺.

c) Pyridine-3-bromo-2-chloro-5-sulphonyl chloride

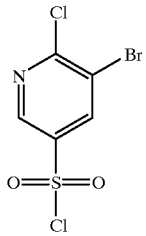

A solution of sodium nitrite (7.6 g, 110.0 mmol) in water (30 ml) was added dropwise to an ice-cooled solution of the product from stage b) (25.3 g, 100.0 mmol) in aqueous hydrochloric acid (115 ml, 20%), so as to maintain the temperature below 6° C. The reaction was stirred for 30 minutes at 0° C. and for a further hour at room temperature. The reaction mixture was evaporated under reduced pressure and the residue dried under vacuum at 70° C. for 72 hours. A mixture of this solid, phosphorus pentachloride (30.0 g, 144 mmol) and phosphorus oxychloride (1 ml, 10.8 mmol) was heated at 125° C. for 3 hours, and then cooled. The reaction mixture was poured onto ice (100 g) and the resulting solid filtered, and washed with water. The product was dissolved in dichloromethane, dried (MgSO$_4$), and evaporated under reduced pressure to afford the title compound as a yellow solid, 26.58 g; δ (CDCl$_3$, 300 MHz): 8.46 (1H, s), 8.92 (1H, s).

d) 3-Bromo-2-chloro-5-(4-ethylpiperazin-1-ylsulphonyl) pyridine

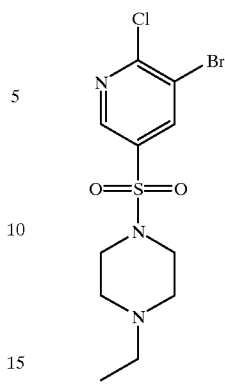

A solution of 1-ethylpiperazine (11.3 ml, 89.0 mmol) and triethylamine (12.5 ml, 89.0 mmol) in dichloromethane (150 ml) was added dropwise to an ice-cooled solution of the product from stage c) (23.0 g, 79.0 mmol) in dichloromethane (150 ml) and the reaction stirred at 0° C. for an hour. The reaction mixture was concentrated under reduced pressure and the residual brown oil was purified by column chromatography on silica gel, using an elution gradient of dichloromethane:methanol (99:1 to 97:3) to afford the title compound as an orange solid, 14.5 g; δ (CDCl$_3$, 300MHz): 1.05 (3H, t), 2.42 (2H, q), 2.55 (4H, m), 3.12 (4H, m), 8.24 (1H, s), 8.67 (1H, s).

e) 3-Bromo-2-ethoxy-5-(4-ethylpiperazin-1-ylsulphonyl) pyridine

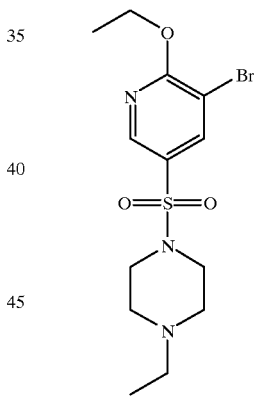

A mixture of the product from stage d) (6.60 g, 17.9 mmol) and sodium ethoxide (6.09 g, 89.55 mmol) in ethanol (100 ml) was heated under reflux for 18 hours, then cooled. The reaction mixture was concentrated under reduced pressure, the residue partitioned between water (100 ml) and ethyl acetate (100 ml), and the layers separated. The aqueous phase was extracted with ethyl acetate (2×100 ml), the combined organic solutions dried (MgSO$_4$) and evaporated under reduced pressure to afford the title compound as a brown solid, 6.41 g; Found: C, 41.27; H, 5.33; N, 11.11. $C_{13}H_{20}BrN_3O_3S$ requires C, 41.35; H, 5.28; N, 10.99%; δ (CDCl$_3$, 300MHz): 1.06 (3H, t), 1.48 (3H, t), 2.42 (2H, q), 2.56 (4H, m), 3.09 (4H, m), 4.54 (2H, q), 8.10 (1H, s), 8.46 (1H, s) LRMS: m/z 378, 380 (M+1)⁺.

f) Pyridine 2-ethoxy-5-(4-ethylpiperazin-1-ylsulphonyl)-3-carboxylic acid ethyl ester

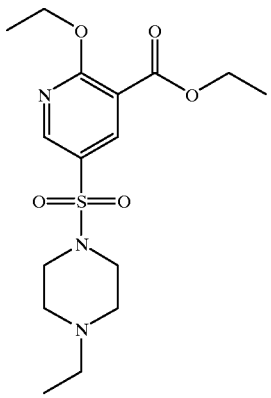

A mixture of the product from stage e) (6.40 g, 16.92 mmol), triethylamine (12 ml, 86.1 mmol), and palladium (0) tris(triphenylphosphine) in ethanol (60 ml) was heated at 100° C. and 200 psi, under a carbon monoxide atmosphere, for 18 hours, then cooled. The reaction mixture was evaporated under reduced pressure and the residue purified by column chromatography on silica gel, using an elution gradient of dichloromethane:methanol (100:0 to 97:3) to afford the title compound as an orange oil, 6.2 g; δ (CDCl$_3$, 300 MHz): 1.02 (3H, t), 1.39 (3H, t), 1.45 (3H, t), 2.40 (2H, q), 2.54 (4H, m), 3.08 (4H, m), 4.38 (2H, q), 4.55 (2H, q), 8.37 (1H, s), 8.62 (1H, s); LRMS: m/z 372 (N+1)$^+$.

g) Pyridine 2-ethoxy-5-(4-ethylpiperazin-1-ylsulphonyl)-3-carboxylic acid

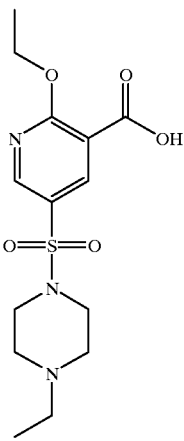

A mixture of the product from stage f) (4.96 g, 13.35 mmol) and aqueous sodium hydroxide solution (25 ml, 2N, 50.0 mmol) in ethanol (25 ml) was stirred at room temperature for 2 hours. The reaction mixture was concentrated under reduced pressure to half it's volume, washed with ether and acidified to pH 5 using 4N hydrochloric acid. The aqueous solution was extracted with dichloromethane (3×30 ml), the combined organic extracts dried (MgSO$_4$) and evaporated under reduced pressure to afford the title compound as a tan coloured solid, 4.02 g; δ (DMSOd$_6$, 300 MHz): 1.18 (3H, t), 1.37 (3H, t), 3.08 (2H, q), 3.17–3.35 (8H, m), 4.52 (2H, q), 8.30 (1H, s) 8.70 (1H, s).

h) 4-[2-Ethoxy-5-(4-ethylpiperazin-1-ylsulphonyl)pyridin-3-ylcarboxamido]-1 H-3-ethylpyrazole-5-carboxamide

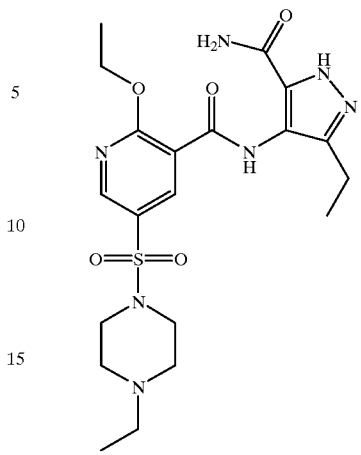

A solution of 4-amino-3-ethyl-1 H-pyrazole-5-carboxamide (WO 9849166) (9.2 g, 59.8 mmol) in N,N-dimethylformamide (60 ml) was added to a solution of the product from stage g) (21.7 g, 62.9 mmol), 1-hydroxybenzotriazole hydrate (10.1 g, 66.0 mmol) and triethylamine (13.15 ml, 94.3 mmol) in dichloromethane (240 ml). 1-(3-Dimethylaminopropyl)-3-ethylcarbodiimide hydrochloride (13.26 g, 69.2 mmol) was added and the reaction stirred at room temperature for 6 hours. The dichloromethane was removed under reduced pressure, the remaining solution poured into ethyl acetate (400 ml), and this mixture washed with aqueous sodium bicarbonate solution (400ml). The resulting crystalline precipitate was filtered, washed with ethyl acetate and dried under vacuum, to afford the title compound, as a white powder, 22 g; δ (CDCl$_3$+1 drop DMSOd$_6$) 0.96 (3H, t), 1.18 (3H, t), 1.50 (3H, t), 2.25–2.56 (6H, m), 2.84 (2H, q), 3.00 (4H, m), 4.70 (2H, q), 5.60 (1H, br s), 6.78 (1H, br s), 8.56 (1H, d), 8.76 (1H d), 10.59 (1H, s), 12.10–12.30 (1H, s); LRMS: m/z 480 (M+1)$^+$.

i) 2-Methoxyethyl-4-[2-ethoxy-5-(4-ethylpiperazin-1-ylsulphonyl)pydridin-3-ylcarboxamidol-3-ethylpyrazole-5-carboxamide

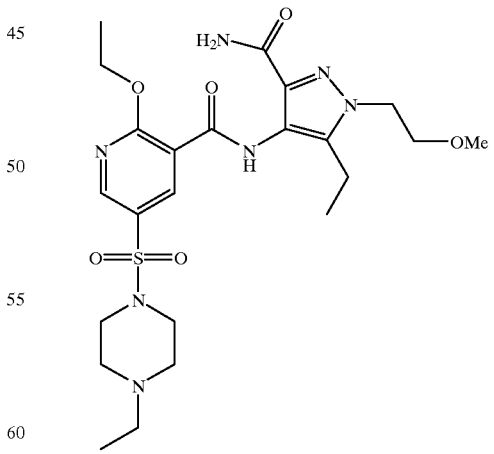

1-Bromo-2-methoxyethane (1.72 mmol) was added to a solution of the product from stage h) (750 mg, 1.56 mmol) and caesium carbonate (1.12 g, 3.44 mmol) in N,N-dimethylformamide (15 ml) and the reaction stirred at 60° C. for 18 hours. The cooled mixture was partitioned between water and ethyl acetate, and the layers separated. The organic layer was dried (MgSO$_4$), concentrated under reduced pressure and azeotroped with toluene to give a solid. This product was recrystallised from ether, to afford the title compound as a white solid.

Example 2

5-[2-iso-Butoxy-5-(4-ethylpiperazin-1-ylsulphonyl) pyridin-3-yl]-3-ethyl-2-(1-methylpiperidin-4-yl)2,6-dihydro-7H-pyrazolo[4,3-d]pyrimidin-7-one

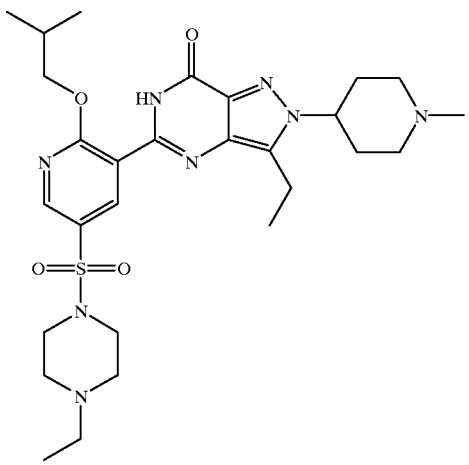

A mixture of the product from stage b) below (90 mg, 0.156 mmol), potassium bis(trimethylsilyl)amide (156 mg, 0.78 mmol) and ethyl acetate (14 mg, 0.156 mmol) in iso-propanol (12 ml) was stirred at 130° C. for 6 hours in a sealed vessel. The cooled reaction mixture was poured into saturated aqueous sodium bicarbonate solution (60 ml), and extracted with ethyl acetate (60 ml). The combined organic extracts were dried (MgSO$_4$), and evaporated under reduced pressure to give a gum. The crude product was purified by column chromatography on silica gel using dichloromethane:methanol:0.88 ammonia (92.6:6.6:0.6) to afford the title compound as a beige foam, 36 mg; δ (CDCl$_3$) 1.01 (3H, t), 1.12 (6H, d), 1.39 (3H, t), 1.94 (2H, m), 2.15 (2H, m), 2.22–2.44 (6H, m), 2.55 (6H, m), 3.02 (4H, m), 3.14 (4H, m) (1H, m), 4.43 (2H, d), 8.60 (1H, d), 9.00 (1H, d), 10.54 (1H, s).

Preparation of Starting Materials a) 2-(1-tert-Butoxycarbonylpiperidin-4-yl)-4-[2-ethoxy-5-(4-ethylpiperazin-1-ylsulphonyl)pyridin-3-ylcarboxamido]-3-ethylpyrazole-5-carboxamide

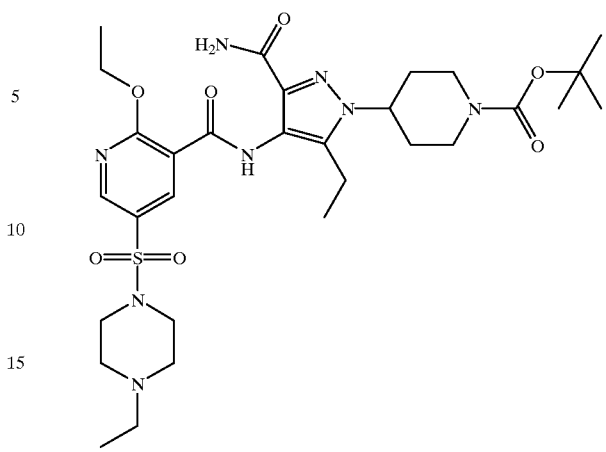

Sodium hydride (64 mg, 60% dispersion in mineral oil, 1.6 mmol) was added to a solution of the product from Example 1, stage h) (1.46 mmol) in tetrahydrofuran (10 ml), and the solution stirred for 10 minutes. tert-Butyl 4-[(methylsulphonyl)oxy]-1-piperidinecarboxylate (WO 9319059) (1.60 mmol) was added and the reaction stirred at 60° C. for 3 days. The cooled mixture was partitioned between ethyl acetate and aqueous sodium bicarbonate solution, and the phases separated. The aqueous layer was extracted with ethyl acetate, the combined organic solutions dried (MgSO$_4$) and evaporated under reduced pressure. The residue was purified by column chromatography on silica gel using dichloromethane:methanol (98:2) as eluant to afford the title compound as a white foam, 310 mg; δ (CDCl$_3$) 1.02 (3H, t), 1.23 (3H, t), 1.49 (9H, s), 1.57 (3H, m), 1.93 (2H, m), 2.16 (2H, m), 2.40 (2H, q), 2.54 (4H, m), 2.82–2.97 (4H, m), 3.10 (4H, m), 4.30 (3H, m), 4.79 (2H, q), 5.23 (1H, s) 6.65 (1H, s), 8.63 (1H, d), 8.82 (1H, d), 10.57 (1H, s).

b) 4-[2-Ethoxy-5-(4-ethylpiperazin-1-ylsulphonyl)pyridin-3-ylcarboxamido]-3-ethyl-2-(1-methylpiperidin-4-yl)pyrazole-5-carboxamide

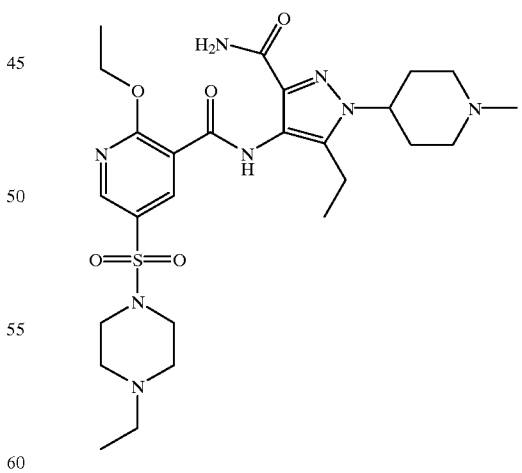

Trifluoroacetic acid (1.5 ml) was added to a solution of the product from stage a) above (320 mg, 0.48 mmol) in dichloromethane (2 ml) and the solution stirred at room temperature for 2½ hours. The reaction mixture was evaporated under reduced pressure and the residue triturated well with ether and dried under vacuum, to provide a white solid.

Formaldehyde (217 microliters, 37% aqueous, 2.90 mmol) was added to a solution of the intermediate amine in dichloromethane (8 ml), and the solution stirred vigorously for 30 minutes. Acetic acid (88 microliters, 1.69 mmol) was added, the solution stirred for a further 30 minutes, then sodium triacetoxyborohydride (169 mg, 0.80 mmol) was added and the reaction stirred at room temperature for 16 hours. The reaction mixture was poured into aqueous sodium bicarbonate solution, and extracted with ethyl acetate. The combined organic extracts were dried (MgSO$_4$) and evaporated under reduced pressure. The residue was purified by column chromatography on silica gel using dichloromethane:methanol:0.88 ammonia (91.75:7.5:0.75) as eluant to afford the title compound, 70 mg; δ (CDCl$_3$) 1.02 (3H, t), 1.22 (3H, t), 1.58 (3H, t), 1.92 (2H, m), 2.14 (2H, m) 2.25–2.45 (7H, m), 2.54 (4H, m), 2.91 (2H, q), 2.99–3.16 (6H, m), 4.08 (1H, m), 4.78 (2H, q), 5.11 (1H, br s), 6.65 (1H, brs), 8.63 (1H, d), 8.83 (1H, d), 10.53 (1H, s).

Example 3

5-[2-Ethoxy-5-(4-ethylpiperazin-1-ylsulphonyl)pyridin-3-yl]3-ethyl-2-phenyl-2,6-dihydro-7H-pyrazolo[4,3-d]pyrimidin-7-one

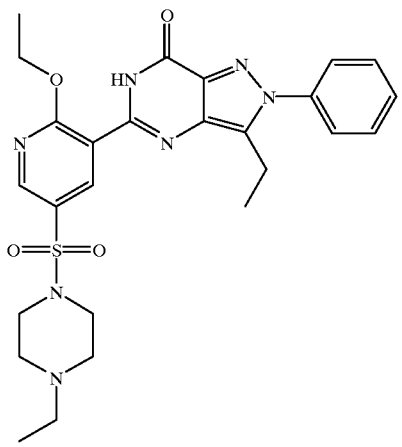

Pyridine (0.1 ml, 1.08 mmol) was added to a mixture of the product from stage a) below (250 mg, 0.54 mmol), copper (II) acetate monohydrate (145 mg, 0.72 mmol), benzeneboronic acid (132 mg, 1.08 mmol) and 4 Å molecular sieves (392 mg) in dichloromethane (5 ml, and the reaction stirred at room temperature for 4 days. The reaction mixture was filtered and the filtrate evaporated under reduced pressure. The crude product was purified by column chromatography on silica gel using dichloromethane:methanol:0.88 ammonia (97:3:0.5) as eluant, and triturated with ether:hexane. The resulting solid was filtered and recrystallised from iso-propanol:dichloromethane to give the title compound as a solid, 200 mg, δ (CDCl$_3$) 1.02 (3H, t), 1.47 (3H, t), 1.60 (3H, t), 2.42 (2H, q), 2.58 (4H, m), 3.10 (2H, q), 3.17 (4H, m), 4.76 (2H, q), 7.40 (1H, m), 7.51 (2H, m), 7.80 (2H, d), 8.67 (1H, d) (1H, s), 10.90 (1H, s); LRMS: m/z 538 (M+1)$^+$.

Preparation of Starting Materials a) 5-[2-Ethoxy-5-(4-ethylpiperazin-1-ylsulphonyl)pyridin-3-yl]-3-ethyl-2,6-dihydro-7H-pyrazolo[4,3-d]pyrimidin-7-one

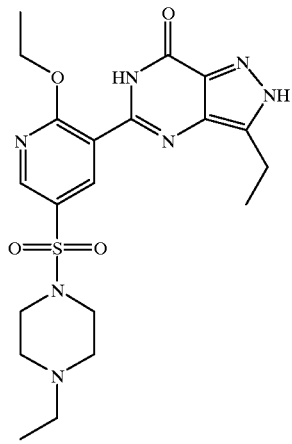

Potassium bis(trimethylsilyl)amide (8.28 g, 41.6 mmol) was added to a solution of the product from Example 1, stage h) (10.0 g, 20.8 mmol) and ethyl acetate (2 ml, 20 mmol) in ethanol (160 ml), and the reaction mixture heated at 120° C. for 12 hours in a sealed vessel. The cooled mixture was evaporated under reduced pressure and the residue was purified by column chromatography on silica gel using dichloromethane:methanol:0.88 ammonia (95:5:0.5) as eluant, to give the title compound, 3.75 g; δ (CDCl$_3$) 1.03 (3H, t), 1.42 (3H, t), 1.60 (3H, t), 2.42 (2H, q), 2.58 (4H, m), 3.02 (2H, q), 3.16 (4H, m), 4.78 (2H, q), 8.66 (1H, d), 9.08 (1H, d), 11.00 (1H, s) 11.05–11.20 (1H, br s), LRMS: m/z 462 (M+1)$^+$.

Example 4

5-(5-Acetyl-2-propoxy-3-pyridinyl)-3-ethyl-2-(1-isopropyl-3-azetidinyl)-2,6-dihydro-7H -pyrazolo[4,3-d]pyrimidin-7-one

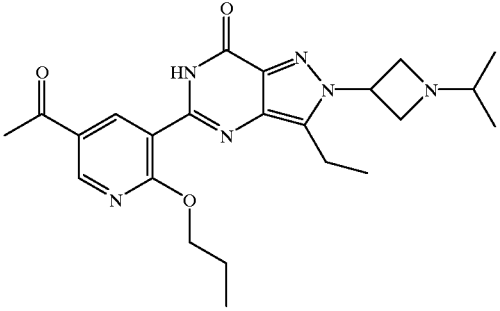

The product from stage h) below (0.23 mmol) was dissolved in dichloromethane (10 ml) and acetone (0.01 ml) was added. After 30 min stirring sodium triacetoxyborohydride (0.51 mmol) was added and stirring continued for 14h. Further acetone (0.01 ml) and sodium triacetoxyborohydride (0.51 mmol) were added and stirring continued for a further 4.5h. Starting material still remained so further acetone (0.01 ml) and sodium triacetoxyborohydride (0.51 mmol) were added and stirring continued for a further 18h. The reaction mixture was diluted with dichloromethane, washed with sodium bicarbonate solution then brine, dried (MgSO$_4$) and concentrated. Purification by flash column chromatography (elution with 94:6:0.6 dichloromethane/methanol/0.88 ammonia) gave the product as a solid, M.p. 162.8–

163.6° C.; 1H NMR (400 MHz, MeOD): δ=1.00 (app. d, 9H), 1.30 (t, 3H), 1.84 (app. q, 2H), 2.60 (s, 3H), 2.62–2.72 (m, 1H), 3.00–3.10 (q, 2H), 3.75 (t, 2H), 3.90 (t, 2H), 4.50 (t, 2H), 5.25 (t, 1H), 8.70 (s, 1H), 8.90 (s, 1H); LRMS (TSP—positive ion) 439 (MH⁺); Anal. Found C, 61.92; H, 6.84; N, 18.70 Calcd for $C_{23}H_{30}O_3N_6 \cdot 0.1CH_2Cl_2$: C, 62.07; H, 6.81; N, 18.80.

Preparation of Starting Materials a) 2-Propoxy-5-iodonicotinic acid

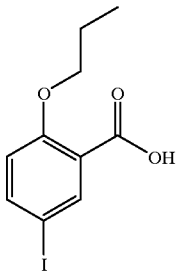

N-Iodosuccinamide (18.22 g, 0.08 mol), trifluoroacetic acid (100 ml) and trifluoroacetic anhydride (25 ml) were added to 2-propoxynicotinic acid (0.054 mol). The mixture was refluxed for 2.5h, cooled and the solvents evaporated. The residue was extracted from water with ethyl acetate and the organics washed with water (twice) and brine (twice), dried ($MgSO_4$) and concentrated. The red residue was redissolved in ethyl acetate washed with sodium thiosulfate solution (twice), water (twice), brine (twice), redried ($MgSO_4$) and concentrated to give the desired product as a solid; ¹H NMR (300 MHz, $CDCl_3$): δ=1.05 (t, 3H), 1.85–2.0 (m, 2H), 4.5 (t, 2H), 8.5 (s, 1H), 8.6 (s, 1H), Analysis: found C, 35.16; H, 3.19; N, 4.46. Calcd for $C_9H_{10}INO_3$: C, 35.19; H, 3.28; N, 4.56%; LRMS (TSP): 529.5 (MH⁺).

b) N-[3-(Aminocarbonyl)-5-ethyl-1 H-pyrazol4-yl]-5-iodo-2-propoxy-nicotinamide

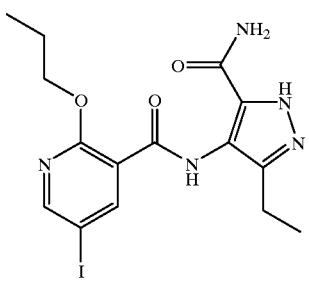

Oxalyl chloride (15.9 mmol) was added to a stirred solution of the product from stage a) (3.98 mmol) in dichloromethane (20 ml) and 3 drops N,N-dimethylformamide added. After 2.5 h the solvent was evaporated and the residue azeotroped 3 times with dichloromethane. The residue was resuspended in dichloromethane (4 ml) and added to a stirred mixture 4-amino-3-ethyl-1H-pyrazole-5-carboxamide (prepared as described in WO 98/49166) (3.58 mmol) and triethylamine (7.97 mmol) in dichloromethane (10 ml). After 1h the solvent was evaporated and the residue partitioned between ethyl acetate and water. The organic phase was separated and washed with 2N HCl (twice), sodium bicarbonate solution (twice) and brine before being dried ($MgSO_4$) and concentrated. The product was triturated with ether and filtered to give the title product as a solid. The mother liquor was concentrated and purified by flash column chromatography (elution with 80% ethyl acetate: hexane) to give further product; ¹H NMR (300MHz, $d_4$-MeOH): δ=1.0 (t, 3H), 1.25 (t, 3H), 1.85–2.0 (m, 2H), 2.8 (q, 2H), 4.5 (t, 2H), 8.5 (s, 1H), 8.6 (s, 1H); LRMS (TSP) 444 (MH⁺).

c) tert-Butyl 3-iodo-1-azetidinecarboxylate

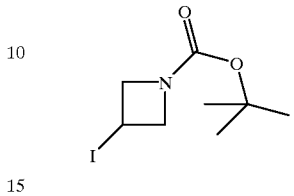

A mixture of tert-butyl 3-[(methylsulfonyl)oxy]-1-azetidinecarboxylate (prepared as described in Synlett 1998, 379; 5.0 g, 19.9 mmol), and potassium iodide (16.5 g, 99.4 mmol) in N,N-dimethylformamide (25 ml), was heated at 100° C. for 42 h. The cooled mixture was partitioned between water and ethyl acetate, and the layers separated. The organic phase was dried over $MgSO_4$, concentrated under reduced pressure and the residue azeotroped with xylene. The crude product was purified by flash column chromatography (dichloromethane as eluant) to give the title compound, 3.26 g; ¹H NMR (300 MHz, $CDCl_3$) δ=1.43 (s, 9H), 4.28 (m, 2H), 4.46 (m, 1H), 4.62 (m, 2H); LRMS (TSP) 284 (MH)⁺ d) tert-Butyl 3-(3-(aminocarbonyl)-5-ethyl-4-{[(5-iodo-2-propoxy-3-pyridinyl)carbonyl]amino}-1 H-pyrazol-1-yl)-1-azetidinecarboxylate

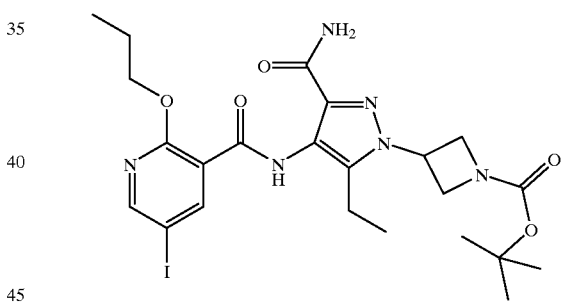

Cesium carbonate (3.59 mmol) was added to a stirred solution of the product from stage b) (1.79 mmol) and the product from stage c) (2.15 mmol) in N,N-dimethylformamide (10 ml) under a nitrogen atmosphere. The mixture was heated at 80° C. for 24 h. The mixture was cooled and extracted from water with ethyl acetate. The organics were dried ($MgSO_4$) and concentrated to give a brown oil. Purification by flash column chromatography (gradient elution from 100% dichloromethane to 90% dichloromethane/MeOH) gave the title product; 1H NMR (400 MHz, DMSO): δ=0.95 (t, 3H), 1.05 (t, 3H), 1.40 (s, 9H), 1.78–1.88 (m, 2H), 2.68 (q, 2H), 4.22–4.35 (m, 4H), 4.40 (t, 2H), 5.3 1H), 7.35 (bs, 1H), 7.52 (bs, 1H), 8.40 (s, 1H), 8.55 (s, 1H), 10.10 (s, 1H); LRMS (TSP—positive ion) 373.2 (MH⁺—BOC and I); Anal. Found C, 45.11; H, 5.07; N, 13.56 Calcd for $C_{23}H_{31}O_5N_6I$. 0.2 DCM: C, 45.28;H, 5.14; N, 13.66.

e) tert-Butyl 3-[3-ethyl-5-(5-iodo-2-propoxy-3-pyridinyl)-7-oxo-6,7-dihydro-2H-pyrazolo[4,3-d]pyrimidin-2-yl]-1-azetidinecarboxylate

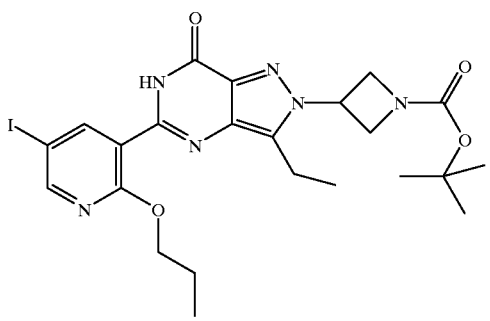

The product from stage d) (28.4 mmol) was dissolved in n-propanol (200 ml), ethyl acetate (6 ml) and potassium t-butoxide (28.4 mmol) were added and the resultant mixture heated to reflux for 6 h. Additional potassium t-butoxide (14.2 mmol) was added and the mixture heated for a further 2 h, after which the solvent was removed in vacuo. The residue was partioned between water (50 ml) and methylene chloride (100 ml) and the organic phase separated. The aqueous phase was extracted with dichloromethane (2×100 ml) and the combined organics dried over $MgSO_4$ and reduced to a solid. Purification by column chromatography (elution with ethyl acetate) gave the title compound; 1H NMR (400MHz, $CDCl_3$): δ=1.05 (t, 3H), 1.30 (t, 3H), 1.43 (s, 9H), 1.87–1.96 (m, 2H), 3.00 (q, 2H), 4.34 (t, 2H), 4.49 (t, 2H), 4.60 (br s, 2H), 5.20 1H), 8.41 (d, 1H), 8.94 (s, 1H), 10.75 (br s, 1H); LRMS (TSP—positive ion) 598.1 ($MNH_4+$); Anal. Found C, 47.54;H, 5.02; N, 14.09 Calcd for $C_{23}H_{29}O_4N_6$: C, 47.60;H, 5.04; N, 14.48.

f) tert-Butyl 3-(3-ethyl-7-oxo-5-{2-propoxy-5-[(trimethylsilyl)ethynyl]-3-pyridinyl}-6,7-dihydro-2H-pyrazolo[4,3-d]pyrimidin-2-yl)-1-azetidinecarboxylate

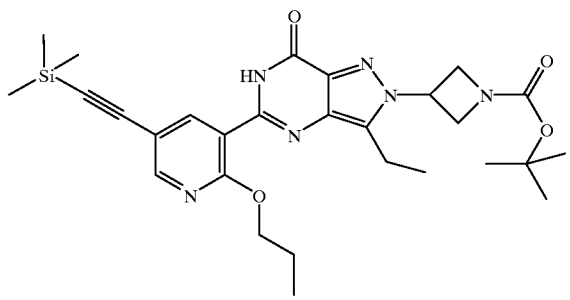

The product from stage e) (0.25 mmol) was suspended in triethylamine (2 ml) and trimethylsilylacetylene (0.39 mmol) and acetonitrile (2 ml to try and solubilise reactants). $Pd(PPh_3)_2Cl_2$ (0.006 mmol) and cuprous iodide (0.006 mmol) were added and the reaction mixture stirred. After 1 h a further portion of trimethylsilylacetylene (0.19 mmol) was added and stirring continued for 2 h. The solvent was evaporated and the residue partitioned between ethyl acetate and water. The organics were washed with brine, dried ($MgSO_4$) and concentrated. Purification by flash column chromatography (gradient elution from 100% dichloromethane to 99% dichloromethane/methanol) gave the title compound; 1H NMR (400MHz, MeOD): δ=0.25 (s, 9H), 1.05 (t, 3H), 1.31 (t, 3H), 1.44 (s, 9H), 1.87–1.96 (m, 2H), 3.00 (q, 2H), 4.33 (t, 2H), 4.52 (t, 2H), 4.54–4.80 (m, 2H), 5.18–5.25 (m, 1H), 8.32 (d, 1H), 8.74 (d, 1H); LRMS (TSP—positive ion) 569 ($MNH_4^+$), 452.0 ($MH^+$); Anal. Found C, 60.82;H, 6.90; N, 15.15 Calcd for $C_{28}H_{38}O_4N_6Si$: C, 61.07;H, 6.95; N, 15.26.

g) tert-Butyl 3-[3-ethyl-5-(5-ethynyl-2-propoxy-3-pyridinyl)-7-oxo-6,7-dihydro-2H-pyrazolo[4,3-d]pyrimidin-2-yl]-1-azetidinecarboxylate

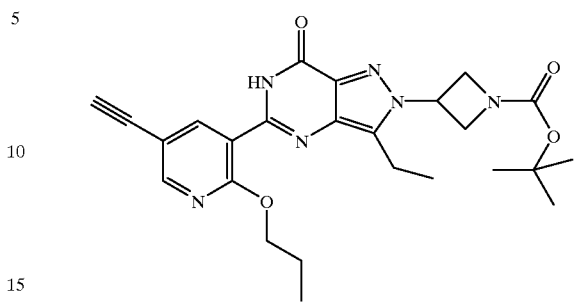

Potassium fluoride (0.38 mmol) was added to a stirred solution of the product of stage f) (0.19 mmol) in aqueous N,N-dimethylformamide (2 ml N,N-dimethylformamide/0.2 ml water) at 0° C. After 10 min the reaction was allowed to warm to room temperature and stirred for 2 h. The reaction mixture was diluted with ethyl acetate and washed with water, 1 N hydrochloric acid (3 times) and brine. The organic layer was dried ($MgSO_4$) and concentrated to give the title compound as a solid; 1H NMR (400MHz, $CDCl_3$): δ=1.05 (t, 3H), 1.30 (t, 3H), 1.43 (s, 9H), 1.88–2.00 (m, 2H), 2H), 3.19 (s, 1H), 4.35 (app t, 2H), 4.52 (app t, 2H), 4.60–4.80 (br s, 2H), 5.22 (t, 1H), 8.39 (s, 1H), 8.80 (s, 1H), 10.75 (br s, 1H); LRMS (TSP—positive ion) 496 ($MNH_4^+$).

h) 5-(5-Acetyl-2-propoxy-3-pyridinyl)-2-(3-azetidinyl)-3-ethyl-2,6-dihydro-7H-pyrazolo[4,3-d]pyrimidin-7-one

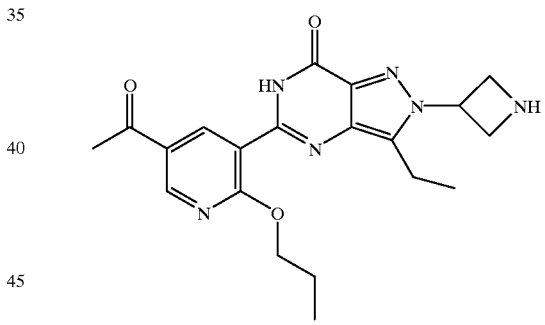

The product from stage g) (1.44 g, 3.0 mmol) in acetone (50 ml) and sulphuric acid (1N, 3 ml) was treated with mercuric sulphate (268 mg, 9.0 mmol) and heated to reflux for 6 h. The reaction mixture was concentrated to ~20 ml in vacuo, poured into sodium bicarbonate (sat. aq., 20 ml) and extracted into methylene chloride (6×20 ml). Combined organics were washed with brine (20 ml), dried over $MgSO_4$, and concentrated to a brown oil which was taken up in 40% trifluoroacetic acid in methylene chloride (50 ml) and water (1 ml) and stirred for 1 h at room temperature. After evaporation in vacuo, the residue was purified by column chromatography (eluting with 95:5:1 methylene chloride:methanol:0.88 ammonia) to afford the title compound as a white hydroscopic foam ( 1.65 g); m.p. 128.5–130.0° C.; 1H NMR (400MHz, MeOD): δ=1.00 (t, 3H), 1.30 (t, 3H), 1.79–1.90 (m, 2H), 2.60 (s, 3H), 3.00–3.10 (q, 2H), 4.50 (t, 2H), 4.60–4.70 (m, 4H), 5.65–5.78 (m, 1H), 8.65 (s, 1 H), 8.90 (s, 1H); LRMS (TSP—positive ion) 397 ($MH^+$).

Example 5

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one

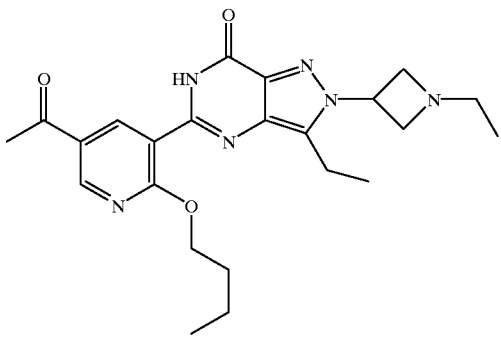

The starting material (120 mg, 0.28 mmol) and cesium carbonate (274 mg, 0.84 mmol) were dissolved in n-butanol (4 ml), and heated at 90° C. under nitrogen with molecular sieves for 96 h. The mixture was then partitioned between water (10 ml) and dichloromethane (10 ml). The organic layer was separated, and the aqueous layer extracted further with dichloromethane (3×15 ml). The combined organic layers were dried (MgSO$_4$), and concentrated in vacuo. The crude product was purified by flash column chromatography (95:5:0.5–90:10:1 ethyl acetate:methanol:0.88 NH$_3$ as eluents), to yield the title compound as a colourless glass (77 mg, 0.18 mmol); m.p. 91.6–93.7° C.; 1H NMR (400 MHz, CDCl$_3$): δ=1.00–1.05 (m, 6H), 1.38 (t, 3H), 1.50–1.62 (m, 2H), 1.90–2.00 (m, 2H), 2.63 (s, 3H),2.63–2.70 (m, 2H), 3.02 (q, 2H), 3.75 (t, 2H), 3.90 (t, 2H), 4.68 (t, 2H), 5.10–5.20(m, 1H, 8.84 (s, 1H), 9.23 (s, 1H), 10.63 (br s,1H); LRMS (TSP—positive ion) 439 (MH$^+$); Anal. Found C, 60.73; H, 7.06; N, 18.03 Calcd for C$_{23}$H$_{30}$O$_3$N$_6$.0.2MeOH.0.1 DIPE: C, 60.88;H, 7.26; N, 17.90.

1.1.1.1.1 Preparation of Starting Materials

5-(5-Acetyl-2-propoxy-3-pyridinyl)-3-ethyl-2-(1-ethyl-3-azetidinyl)-2,6-dihydro-7H-pyrazolo[4,3-d]pyrimidin-7-one

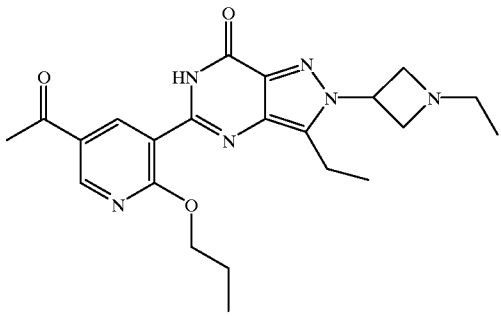

Sodium cyanoborohydride (92 mg, 1.47 mmol) was added to a stirred solution of the product from Example 4 stage h) (500 mg, 0.98 mmol) and sodium acetate (161 mg, 1.96 mmol) in methanol (10 ml) under nitrogen at room temperature. After 1 h the mixture was poured into NaHCO$_3$ (sat. aq., 20 ml), and extracted with dichloromethane (3×15 ml). The combined organic layers were dried (MgSO$_4$) and concentrated in vacuo. The crude product was purified by flash column chromatography (95:5:0.5–80:20:1 ethyl acetate:methanol:0.88 NH$_3$ as eluent) to yield the title compound as a white solid (140 mg, 0.33 mmol); 1H NMR (400 MHz, CDCl$_3$): δ=0.97 (t, 3H), 1.03 (t, 3H), 1.30 (t, 3H), 2.82–2.97 (m, 2H), 2.58–2.65 (m, 5H), 2.98 (q, 2H), 3.68 (t, 2H), 3.85 (dd, 2H), 4.58 (dd, 2H), 5.05–5.17 (m, 1H), 8.79 (s, 1H), 9.18 (s, 1H), 10.62 (br s, 1H); LRMS (TSP—positive ion) 426 (MH$^+$).

Also preferred as cGMP PDE$_V$ inhibitors are compounds disclosed in PCT/EP95/00183, published as WO 95/19978 and which designates, inter alia, the United States, herein incorporated by reference, said compounds having the formula (VII):

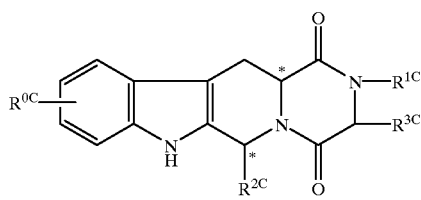

(VII)

and salts and solvates thereof, in which:

$R^{0C}$ represents hydrogen, halogen or C$_1$–C$_6$alkyl,;

$R^{1C}$ represents hydrogen, C$_1$–C$_6$alkyl, C$_2$–C$_6$alkenyl, C$_2$–C$_6$alkynyl, haloC$_1$–C$_6$alkyl, C$_3$–C$_8$cycloalkyl, C$_3$–C$_8$cycloalkylC$_1$–C$_3$alkyl, arylC$_1$–C$_3$alkyl or heteroarylC$_1$–C$_3$alkyl;

$R^{2C}$ represents an optionally substituted monocyclic aromatic ring selected from benzene, thiophene, furan and pyridine or an optionally substituted bicyclic ring

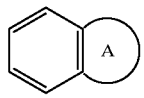

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^{3C}$ represents hydrogen or C$_1$–C$_3$alkyl, or $R^{1C}$ and $R^{3C}$ together represent a 3- or 4-membered alkyl or alkenyl ring.

A preferred subset of compounds having formula VIIa (also disclosed in WO 95/19978) includes compounds of the formula:

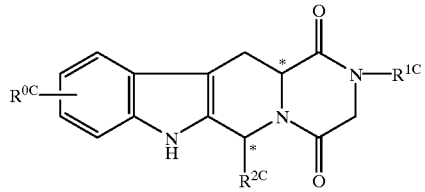

(VIIa)

and salts and solvates thereof, in which:

$R^{0C}$ represents hydrogen, halogen or C$_1$–C$_6$alkyl;

$R^{1C}$ represents hydrogen, C$_1$–C$_6$alkyl, haloC$_1$–C$_6$alkyl, C$_3$–C$_8$cycloalkyl, $C_3$–$C_8$cycloalkyl-$C_1$–$C_3$alkyl, aryl$C_1$–$C_3$alkyl or heteroaryl$C_1$–$C_3$alkyl; and $R^{2C}$ represents an optionally substituted monocyclic aromatic ring selected from benzene, thiophene, furan and pyridine or an optionally substituted bicyclic ring

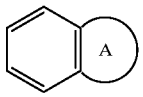

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen.

Oral daily dosages of the above cGMP elevators can range from about 1 mg to about 200 mg with a preferred range of from about 20 mg to about 100 mg. Dosage is ad libitum from about 15 minutes to about 4 hours prior to sexual activity. Dosages and timing of dosing can be adjusted for topical dosage forms such as creams or aerosols. cGMP elevators of the present invention include produgs, stereoisomers, hydrates, tautomers and salts of the described compounds. The cGMP elevators of the present invention may be formulated and administered as described for the estrogen agonists/antagonists above.

The cGMP PDE inhibitors useful in this invention as cGMP elevators may be chosen from among any of those already known to the art or subsequently discovered and/or hereafter developed. Suitable cGMP PDE inhibitors include those disclosed in any of the following U.S. Patents:

a 5-substituted pyrazolo[4,3-d]pyrimidine-7-one as disclosed in U.S. Pat. No. 4,666,908;

a griseolic acid derivative as disclosed in any of U.S. Pat. Nos. 4,634,706, 4,783,532, 5,498,819, 5,532,369, 5,556,975, and 5,616,600;

a 2-phenylpurinone derivative as disclosed in U.S. Pat. No. 4,885,301;

a phenylpyridone derivative as disclosed in U.S. Pat. No. 5,254,571;

a fused pyrimidine derivative as disclosed in U.S. Pat. No. 5,047,404;

a condensed pyrimidine derivative as disclosed in U.S. Pat. No. 5,075,310;

a pyrimidopyrimidine derivative as disclosed in U.S. Pat. No. 5,162,316;

a purine compound as disclosed in U.S. Pat. No. 5,073,559;

a quinazoline derivative as disclosed in U.S. Pat. No. 5,147,875;

a phenylpyrimidone derivative as disclosed in U.S. Pat. No. 5,118,686;

an imidazoquinoxalinone derivative or its aza analog as disclosed in U.S. Pat. Nos. 5,055,465 and 5,166,344;

a phenylpyrimidone derivative as disclosed in U.S. Pat. No. 5,290,933;

a 4-aminoquinazoline derivative as disclosed in U.S. Pat. No. 5,436,233 or 5,439,895;

a 4,5-dihydro-4-oxo-pyrrolo[1,2-a]quinoxaline derivative as disclosed in U.S. Pat. No. 5,405,847;

a polycyclic guanine derivative as disclosed in U.S. Pat. No. 5,393,755;

a nitogenous heterocyclic compound as disclosed in U.S. Pat. No. 5,576,322;

a quinazoline derivative as disclosed in U.S. Pat. No. 4,060,615;

a 6-heterocyclyl pyrazolo[3,4-d]pyrimidin-4-one as disclosed in U.S. Pat. No. 5,294,612; and a 4-aminoquinazoline derivative as disclosed in U.S. Pat. No. 5,436,233;

Other disclosures of cGMP PDE inhibitors include the following, all of which are herein incorporated by reference:

European patent Application (EPA) publication no. 0428268;

European patent 0442204;

International patent application publication no. WO 94/19351;

Japanese patent application 5–222000;

European Journal of Pharmacology, 251, (1994), 1;

International patent application publication no. WO 94/22855;

a pyrazolopyrimidine derivative as disclosed in European patent application 0636626;

a 4-aminopyrimidine derivative as disclosed in European patent application 0640599;

an imidazoquinazoline derivative as disclosed in International patent application W095/06648;

an anthranilic acid derivative as disclosed in International patent application W095/18097;

a tetracyclic derivative as disclosed in International patent application W095/19978;

an imidazoquinazoline derivative as disclosed in European patent application 0668280; and a quinazoline compound as disclosed in European patent application 0669324.

The cGMP PDE inhibition of a compound can be determined by standard assays known to the art, for example as disclosed in U.S. Pat. No. 5,250,534. Compounds which are selective inhibitors of cGMP PDE relative to cAMP PDE are preferred, and determination of such compounds is also taught in U.S. Pat. No. 5,250,534. Particularly preferred are compounds which selectively inhibit the $PDE_V$ isoenzyme, as disclosed in the aforementioned PCT/EP94/01580, published as WO 94/28902.

Advantageously, the present invention also provides a kit for use by a consumer afflicted with or susceptible to conditions responsive to testosterone elevation such as male subject sexual dysfunction, decreased libido in female subjects including post-menopausal women or timidity in female subjects including post-menopausal women. The kits comprise a) a pharmaceutical composition comprising an estrogen agonist/antagonist and a pharmaceutically acceptable carrier, vehicle or diluent; and b) instructions describing a method of using the pharmaceutical composition for treating conditions that are responsive to the elevation of testosterone levels in the body. The instructions may also indicate that the kit is for the treatment of testosterone-responsive conditions while substantially reducing the concomitant liability of adverse effects associated with testosterone administration. The conditions responsive to testosterone elevation include male subject sexual dysfunction and timidity in female subjects including post-menopausal women and the increase of libido in female subjects including post-menopausal women. This invention also provides a kit for the treatment of male subject sexual dysfunction comprising a therapeutically effective amount of an estrogen agonist/antagonist and a pharmaceutically acceptable carrier, vehicle or diluent in a first unit dosage form and, optionally, a) a therapeutically effective amount of a cGMP elevator either formulated in the same pharmaceutical composition as the estrogen agonist/antagonist or formulated in a separate pharmaceutical composition with a pharmaceutically acceptable carrier, vehicle or diluent in a second unit dosage form.

A "kit" as used in the instant application includes a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It is desirable to provide a written memory aid, where the written memory aid is of the type containing information and/or instructions for the physician, pharmacist or patient, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday,". . . etc. "Second Week, Monday, Tuesday,.". . . etc. Other variations of memory aids will be readily apparent. A "daily dose" can be a single tablet or capsule or several tablets or capsules to be taken on a given day. When the kit contains separate compositions, a daily dose of another one or more compositions of the kit can consist of one tablet or capsule while a daily dose of another one or more compositions of the kit can consist of several tablets or capsules.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Methods of preparing various pharmaceutical compositions with a certain amount of active ingredient are known, or will be apparent in light of this disclosure, to those skilled in this art. For examples, see *Remington's Pharmaceutical Sciences*, Mack Publishing Company, Easton, Pa.,19th Edition (1995).

Pharmaceutical compositions according to the invention may contain 0.001%–95% of the compound(s) of this invention. In any event, the composition or formulation to be administered will contain a quantity of a compound(s) according to the invention in an amount effective to treat the condition or disease of the subject being treated.

Based on a reading of the present description and claims, certain modifications to the compositions and methods described herein will be apparent to one of ordinary skill in the art. The claims appended hereto are intended to encompass these modifications.

All references and patents cited herein are incorporated by reference.

EXAMPLES

Example 1

Measurement of Libido in Post-menopausal Women

Enhancement of libido in post-menopausal women is evaluated in a 12 week, placebo-controlled clinical study using the Women's Health Questionnaire (WHQ) as the measurement technique. Prior to the commencement in the study, post-menopausal women are divided into two groups of between 5 and 100 women in each group. One group is a placebo control group. The other group is a test group that receives a pharmaceutical composition containing an estrogen agonist/antagonist. At the start of the study, all participants in both groups complete a WHQ. Participants in the control group receive a daily placebo composition. Participants in the test group receive a composition containing an estrogen agonist/antagonist. At the end of the study, participants in both groups again complete the WHQ. The results of the WHQ from the control group and the test group are then compared.

The Women's Health Questionnaire (WHQ) provides a detailed examination of minor psychological and somatic symptoms experienced by per- and postmenopausal women (Hunter M., et al., *Maturitas;* 8: 217, 1986). The WHQ is well documented in terms of reliability and validity. The questionnaire has 36 questions rated on four-point scales. The higher the score, the more pronounced is the distress and dysfunction. The 36 items combine into nine factors describing somatic symptoms, depressed mood, cognitive difficulties, anxiety/fear, sexual functioning, vasomotor symptoms, sleep problems, menstrual symptoms and attraction.

Example 2

Pharmacological Testing of Treatment for Male Subject Sexual Dysfunction

Adult male Sprague-Dawley rats are used for this study. Animals are maintained singly in wire-bottom cages under controlled light (14 hour light, 10 hour dark) and temperature. Animals receive Purina rat chow and tap water ad libitum.

All animals are tested for sexual behavior prior to orchidectomy and estrogen agonist/antagonist compound administration. The test male is placed into a testing arena for 5 minutes prior to the introduction of a female via the top of the chamber. The stimulus female (ovariectomized) is rendered sexually receptive by a subcutaneous (s.c.) injection of 100 microgram of estradiol benzoate and 500 microgram of progesterone in 0.1 ml of corn oil, 48 and 4 hours prior to testing. Each mount, intromission and ejaculation is recorded. Each male is tested every 5 days until four successive and consistent behavioral patterns are achieved. In addition to copulatory tests, males are tested for penile erection reflexes (Davidson et al, *Physiology & Behavior*; 21:171, 1978). Erectile tests are performed 24 hours before copulatory events every 5 days. After copulatory behavior parameters are deemed satisfactory, animals are bilaterally orchidectomized via a single mid-ventral incision and rehoused for 28 days with no further behavioral testing.

Rats are randomly divided among experimental groups, they receive a dose of estrogen agonist/antagonist or vehicle alone as a control via single or multiple tail vein injections prior to retesting. Testing is performed as described above and the following parameters are calculated from the record: mount latency (ML), the time from the introduction of the female to the initial mount or intromission; intromission latency (IL), the time from the introduction of the female to the first intromission; ejaculation latency (EL), the time from the first intromission to ejaculation; and postejaculatory interval (PEI), the time from ejaculation to the first intromission of the next copulatory series. Tests are terminated and considered negative if intromission latency exceeds 15 minutes, ejaculation latency exceeds 30 minutes or postejaculatory interval exceeds 15 minutes. Mounting frequency and intromission frequency are also assessed. Copulatory and penile reflex tests are performed at 3, 7, 14, 21, 28, 35 and 42 days after administration of the compounds.

Records of the study are kept and at the end of the study the results are compared. Activity of the compositions and methods of the invention are illustrated by positive effects in the above assay.

Example 3

Testosterone Elevation

In a random, double-blind, parallel group, placebo-controlled study, 3-{1-[4-(2-dimethylamino-ethoxy)-phenyl]-2-phenyl-but-enyl}-phenol was administered to men, aged 72 to 84 with below average serum testosterone levels. Subjects received either placebo or 3-{1-[4-(2-dimethylamino-ethoxy)-phenyl]-2-phenyl-but-enyl}-phenol as a sequential escalating dose, with subjects receiving 20 mg daily for the first month, 40 mg daily for the second month, and 60 mg daily for the final four months (remainder) of the study. Total serum testosterone was determined in the subjects at 4 weeks and at 2, 3 and 6 months. The results in Table 1 show a significant increase in total serum testosterone in subjects receiving 3-{1-[4-(2-dimethylamino-ethoxy)-phenyl]-2-phenyl-but-enyl}-phenol as the treatment compound over subjects receiving placebo during the study (p=0.026).

TABLE 1

Mean Percent Change From Baseline in Testosterone

| | Placebo | | | Treatment Compound | | |
|---|---|---|---|---|---|---|
| | % Change | Standard Deviation | Number of Subjects | % Change | Standard Deviation | Number of Subjects |
| Week 4 | 13.23 | 38.91 | 16 | 36.20 | 28.03 | 15 |
| 2 Months | 15.78 | 31.97 | 17 | 44.45 | 25.85 | 13 |
| 3 Months | 4.29 | 26.49 | 17 | 41.47 | 29.00 | 14 |
| 6 Months | 9.25 | 43.95 | 16 | 45.19 | 30.32 | 13 |

What is claimed is:

1. A method of treating premature ejaculation in a male, the method comprising the step of administering to a patient experiencing premature ejaculation an effective amount of (−)-cis-6-phenyl-5-[4-(2-pyrrolidin-1-yl-ethoxy)-phenyl]-5,6,7,8-tetrahydro-naphthalene-2-ol, or a nontoxic pharmaceutically acceptable acid addition salt, N-oxide, ester quaternary ammonium salt or prodrug thereof.

2. The method of claim 1 wherein the (−)-cis-6-phenyl-5-[4-(2-pyrrolidin-1-yl-ethoxy)-phenyl]-5,6,7,8-tetrahydro-naphthalene-2-ol is in the form of the tatrate salt.

3. A method of treating premature ejaculation in a male, the method comprising the step of administering to a patient experiencing premature ejaculation an effective amount of (−)-cis-6-phenyl-5-[4-(2-pyrrolidin-1-yl-ethoxy)-phenyl]-5,6,7,8-tetrahydro-naphthalene-2-ol, or a nontoxic pharmaceutically acceptable acid addition salt, N-oxide, ester quaternary ammonium salt or prodrug thereof, and an elevator of cyclic guanosine 3', 5'-monophosphate.

4. The method of claim 3 wherein the (−)-cis-6-phenyl-5-[4-(2-pyrrolidin-1-yl-ethoxy)-phenyl]-5,6,7,8-tetrahydro-naphthalene-2-ol is in the form of the tatrate salt.

5. The method of claim 3 wherein the elevator of cyclic guanosine 3', 5'-monophosphate is sildenafil citrate.

* * * * *